(12) United States Patent
Pierce et al.

(10) Patent No.: US 6,890,568 B2
(45) Date of Patent: May 10, 2005

(54) METHOD FOR MANAGEMENT OF BLOOD GLUCOSE LEVELS

(76) Inventors: Grant Pierce, 194 Foxmeadow Drive, Winnipeg, Manitoba (CA), R3P 1T3; Clayton Heyliger, 1206 Wolseley Ave., Winnipeg, Manitoba (CA), R3G 1G7

( * ) Notice: Subject to any disclaimer, the term of this patent is extended or adjusted under 35 U.S.C. 154(b) by 0 days.

(21) Appl. No.: 10/244,610

(22) Filed: Sep. 17, 2002

(65) Prior Publication Data

US 2003/0108625 A1 Jun. 12, 2003

Related U.S. Application Data

(63) Continuation-in-part of application No. 09/576,130, filed on May 22, 2000, now abandoned.
(60) Provisional application No. 60/135,653, filed on May 24, 1999.

(51) Int. Cl.$^7$ .......................... A61K 35/78; A61K 9/00; A61K 33/08; A01N 25/00
(52) U.S. Cl. ...................... 424/729; 424/400; 424/646; 514/866; 514/884
(58) Field of Search ................................. 424/400, 646, 424/729; 514/866, 884

(56) References Cited

U.S. PATENT DOCUMENTS

| | | | | |
|---|---|---|---|---|
| 5,338,759 A | * | 8/1994 | Shechter et al. ............ | 514/492 |
| 5,910,308 A | | 6/1999 | D'Jang | |
| 6,129,924 A | * | 10/2000 | Maurel et al. .............. | 424/400 |

FOREIGN PATENT DOCUMENTS

| | | | |
|---|---|---|---|
| CN | 1142905 | * | 2/1997 |
| CN | 1149405 | | 2/1997 |
| FR | 2695390 | | 3/1994 |
| WO | WO94/06809 | | 3/1994 |
| WO | WO98/01461 | * | 1/1998 |

OTHER PUBLICATIONS

Gruenwald, J. et al (eds.). PDR for Herbal Medicines. 1998. Medical Economics company, Montvale, N.J., p. 710.*
Spraycar (, M. (editor). Stedman's Medical Dictionary. 1995. Williams and Wilkins, Baltimore, p. 1134, col. 2, Lines 9–14.*
PDR for Herbal Medicine, 1998, Medical Economics Company, N.J., pp. 710–711.
The Complete German Commission E Monographs: Therapeutic Guide to Herbal Medicine, Bluementhal, M. and Busse, W.R. (Eds.) American Botanical Council. Austin, Texas in Cooperation with Integrative Medicine Communications, Boston, MA, p. 366.

* cited by examiner

*Primary Examiner*—Ralph Gitomer
*Assistant Examiner*—Kailash C. Srivastava
(74) *Attorney, Agent, or Firm*—Michael R. Williams; Adrian D. Battison; Ryan W. Dupuis

(57) ABSTRACT

A composition for managing blood glucose levels is herein described. The composition comprises decocted tea and vanadate and does not cause the same side effects as vanadate and water mixtures known in the prior art. Specifically, the vanadate suspended in decocted tea does not cause diarrhea and in some cases stabilizes blood glucose at normal levels for several weeks after only a few treatments.

5 Claims, 27 Drawing Sheets

METHOD FOR MANAGEMENT OF BLOOD GLUCOSE LEVELS

This application is derived from Provisional Patent Application Ser. No. 60/135,653 filed on May 24, 1999 and is a continuation-in-part of U.S. Ser. No. 09/576,130, filed May 22, 2000 now abandoned.

FIELD OF THE INVENTION

The present invention relates generally to a pharmaceutical composition. More specifically, the present invention relates to a pharmaceutical composition for managing blood glucose levels.

BACKGROUND OF THE INVENTION

Since the discovery of insulin by Banting and Best, regular insulin injections have remained the best and most frequently used therapy to control abnormal blood glucose levels in diabetic patients (Pierce et al in *Heart Dysfunction in Diabetes* (CRC Press: Boca Raton, Fla., 1988). The use of insulin has significantly prolonged the life of diabetic patients and reduced the severity of many complications associated with this disease. Besides insulin, only the sulfonylurea drugs have gained widespread use for the control of diabetes (Pierce et al, 1988).

Despite the acceptance of insulin and sulfonylurea drugs as effective therapies, there are significant limitations inherent in their use. For example, sulfonylurea drugs are usually used only in cases of mild diabetes. Furthermore, insulin injections, although effective, are not an optimum way of controlling the disease. This is due to the fact that daily injections with needles is painful and unpleasant. Unfortunately, other means of delivering insulin, for example, implanted mini-pumps and islet transplantation, have not evolved to a point where they could be considered viable replacements for daily injections of insulin (Pierce et al, 1988).

As a consequence, there has been considerable effort expended searching for insulin-mimetic compounds. For example, vanadate was identified over 10 years ago as a replacement for insulin (Heyliger et al, 1985, *Science* 227: 1474). Therein, vanadate was shown to control diabetes in an insulin-deficient, streptozotocin-induced rat model of diabetes (Heyliger et al, 1985). Specifically, vanadate was included in the drinking water of the rats, thus removing the need for unpleasant injections (Heyliger et al, 1985). However, there were three important limitations in this methodology: first, the animals began to stop drinking the water containing vanadate; second, it was difficult to regulate and quantitate the amount of vanadate being administered to the rats in this manner; and third, and most importantly, the animals developed a life-threatening diarrhea when the vanadate was administered in this manner. Other complications accompanying the severe diarrhea included weight loss, depressed appetite, neurological disorders, liver cytotoxicity and death (Mongold et al, 1990, *Pharm Tox* 67: 192–198; Domingo et al, 1995, *Mol Cell Bio* 153: 233–240; Malabu et al, 1994, *Diabetes* 43: 9–15; Llobet and Domingo, 1984, *Tox Letters* 23: 227–231; Domingo et al, *Pharm Tox* 68: 249–253).

Thus, although vanadate was considered a potentially important therapy for controlling diabetes, the side-effects associated with its administration have been so serious as to preclude any clinical use.

Some laboratories have attempted to circumvent the gastrointestinal complications by developing vanadate analogues (Aharon et al, 1998, *Diabetes Care* 21: 2194; Halberstam et al, 1996, *Diabetes* 45: 659–666; Goldfine et al, 1995, *J Clin Endocrinol Metab* 80: 3312–3320) that would increase the hypoglycemic action while limiting the harmful side effects, that is, the generation of diarrhea. An example is vanadyl sulfate (Aharon et al, 1998). However, to our knowledge, no vanadate analogues have successfully addressed the problem in a manner that would make these compounds useful in a clinical setting. The central problem remains: ingestion of vanadate induces severe diarrhea and other toxic complications (Shechter, 1990, *Diabetes* 39: 1–5; Mongold et al, 1990; Domingo et al, 1995; Malabu et al, 1994; Llobet and Domingo, 1984; Domingo et al, 1991). However, "the idea of having an insulin-mimetic agent capable of utilizing an alternative pathway is very attractive, as discussed earlier. This is especially true if the substance can be administered orally. Studies should continue to elucidate the level of vanadate toxicity over prolonged treatment and to search for agents that can be coadministered with vanadate and reduce the dosage required to achieve normoglycemia" (Shechter, 1990).

Clearly, a method for orally administering vanadate without the side-effects discussed above is needed. Similarly, an orally-administered pharmaceutical composition for treating diabetes comprising an insulin-mimetic agent such as vanadate and a suitable carrier such that side-effects are minimized is needed.

SUMMARY OF THE INVENTION

According to a first aspect of the invention, there is provided a method of preparing a mixture for lowering levels of blood glucose to normoglycemia comprising:

providing black tea, jasmine tea or Japanese green tea;

adding the tea to boiling water;

boiling the tea, thereby producing a decocted tea;

cooling the decocted tea; and suspending a quantity of vanadate in the decocted tea.

According to a second aspect of the invention, there is provided a pharmaceutical composition comprising a therapeutically effective amount of vanadate suspended in decocted black tea, jasmine tea or Japanese green tea for lowering levels of blood glucose in an individual to normoglycemia.

According to a third aspect of the invention, there is provided a method comprising:

administering to an individual in need thereof a pharmaceutical composition comprising a therapeutically effective amount of vanadate suspended in decocted black tea, jasmine tea or Japanese green tea thereby lowering levels of blood glucose in the individual to normoglycemia.

Figure 1:
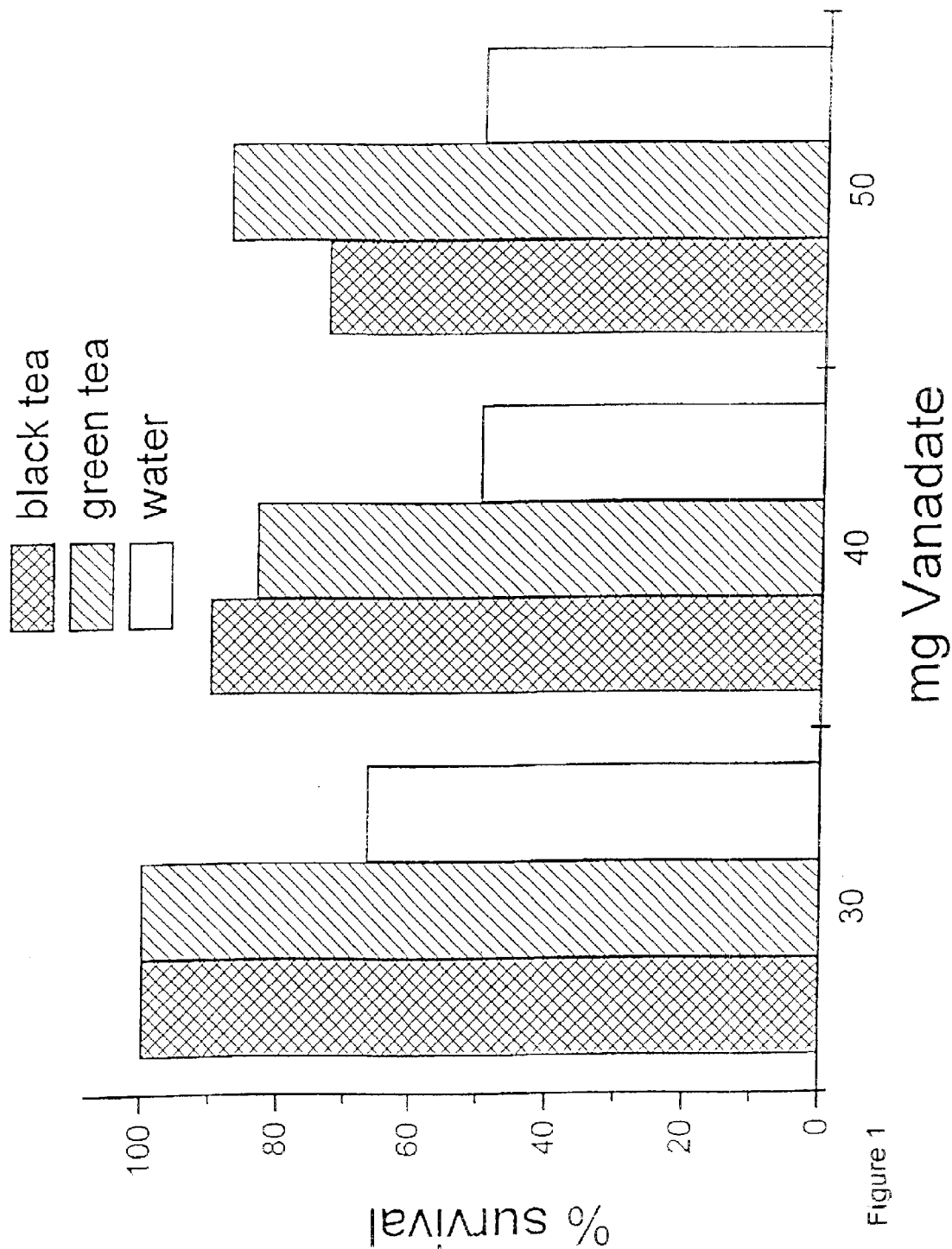
FIG. 1 is a bar graph of percent survival of subjects administered varying quantities of vanadate suspended in black tea, green tea and water.

TABLE 1 summarizes results of subjects administered 30 mg of vanadate suspended in water.

TABLE 2 summarizes results of subjects administered 40 mg of vanadate suspended in water.

TABLE 3 summarizes results of subjects administered 50 mg of vanadate suspended in water.

TABLE 4 summarizes results of subjects administered 30 mg of vanadate suspended in green tea.

TABLE 5 summarizes results of subjects administered 40 mg of vanadate suspended in green tea.

TABLE 6 summarizes results of subjects administered 50 mg of vanadate suspended in green tea.

TABLE 7 summarizes results of subjects administered 30 mg of vanadate suspended in black tea.

TABLE 8 summarizes results of subjects administered 40 mg of vanadate suspended in black tea.

TABLE 9 summarizes results of subjects administered 50 mg of vanadate suspended in black tea.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated herein by reference.

Definitions

As used herein, "gastrointestinal soothing tea" refers to any tea known in the art as a remedy for GI distress.

As used herein, "decocted tea" refers to a concentrated tea extract containing medicinal constituents of the tea obtained by simmering dried tea leaves and other parts in boiling water.

Described herein is a method of utilizing vanadate as an effective insulinomimetic agent while preventing the vanadate-induced gastrointestinal distress (diarrhea) associated with administration of vanadate. Specifically, the vanadate was suspended in a decoction of specific teas, which were chosen based on their reputed abilities to prevent or treat gastrointestinal problems like diarrhea. The teas were prepared to generate a highly concentrated decoction as described below and the vanadate was suspended therein. As discussed below, the decocted tea and vanadate mixtures lowered blood glucose levels of test animals to normal levels, in some cases for an extended period of time, with fewer side effects, compared to administered doses of a water and vanadate mixture. It was hypothesized that the tannin or high antioxidant content of the teas, or another specific component of the tea would be enriched in this decoction in such a manner as to avoid the diarrhea side-effects and enhance the hypoglycemic action of vanadate. The data indicates that elements in the tea are counteracting the harmful effects of vanadate, possibly by modifying the vanadate in some way, as discussed below. Clearly, pharmaceutical compositions based on the decocted tea and vanadate mixture may have long-term hypoglycemic effects, thereby obviating the need for daily insulin injections to treat diabetes and/or control blood glucose levels.

Preferably, the decocted tea is selected from the group consisting of black tea, jasmine tea, Japanese green tea and mixtures thereof.

Clearly, the decocted tea is lessening the side effects of vanadate. The tea may modify the vanadate into something more palatable to the gut. For example, once the vanadate is added to the tea, the mixture slowly darkens over a 24 hour period. This is similar to the darkening seen when iron is added to tea which is thought to be caused by the formation of soluble and insoluble complexes within the tea. It is possible that a similar reaction is occurring with the vanadate and tea. Alternatively, the antioxidant content of the tea may be altering the redox potential of the vanadate. Or, the tea may instead act upon the gut itself and have no important interactions with the vanadate. For example, it is known tea inhibits gut motility—this may deter the diarrhea effects of vanadate and allow the vanadate to cross the gut wall at the same time. Most of these effects have been attributed to its tannin content.

Furthermore, the decocted tea mixture is also enhancing the normoglycemic properties of vanadate, as blood glucose levels are stabilized for longer periods of time following treatment.

Clearly, the active ingredients of these mixtures or synthetic preparations thereof could be used to develop pharmaceutical compositions for managing blood glucose levels and treating diabetes in humans using methods known in the art. Specifically, a therapeutically effective amount of the decocted tea/vanadate mixture may be combined with pharmaceutically acceptable carriers and/or excipients. In other embodiments, the decocted tea/vanadate mixture may be lyophilized and, for example, combined with binders to form a tablet or inserted into caplets.

The invention provides kits for carrying out the methods of the invention. Accordingly, a variety of kits are provided. The kits may be used for any one or more of the following: treating diabetes in an individual; or maintaining blood glucose levels in an individual.

The kits of the invention comprise one or more containers comprising vanadate suspended in a decocted tea as described above or lyophilized vanadate suspended in a decocted tea and a set of instructions, generally written instructions although electronic storage media (e.g., magnetic diskette or optical disk) containing instructions are also acceptable, relating to the use and dosage of the vanadate suspended in decocted tea for the intended treatment (e.g., treating diabetes or maintaining blood glucose levels). The instructions included with the kit generally include information as to dosage, dosing schedule, and route of administration for the intended treatment. The containers of vanadate suspended in decocted tea may be unit doses, bulk packages (e.g., multi-dose packages) or sub-unit doses.

The vanadate suspended in decocted tea of the kit may be packaged in any convenient, appropriate packaging. For example, if the vanadate suspended in decocted tea is a freeze-dried formulation, an ampoule with a resilient stopper is normally used, so that the drug may be easily reconstituted by injecting fluid through the resilient stopper.

The following Examples are provided to illustrate, but not limit, the invention. In the examples discussed herein, black tea, green tea and raspberry tea were decocted. Specifically, the black tea used was China Lichee Black Tea (Golden Sail Brand) produced by China Tuhsu Guangdong Tea Import and Export Corporation, Golden Sail Brand, China; and the green tea was Japanese Green Tea, produced by Ujinotsuyu-Aoyanagi Midori Tea Company, Japan. For the HPLC studies discussed below, Chinese Green Tea, produced by Golden Dragon and Red Raspberry Leaf Tea produced by The Canadian Herbal Tea Company, PO Box 20024, Selkirk, MB, Canada, R1A 1S0 were also used, as described below. As will be appreciated by one skilled in the art, other teas having similar properties, that is, tannin and/or high antioxidant concentrations and/or reputed gastrointestinal soothing properties may also be suitable.

In an illustrative example, the decoction of tea was prepared as follows: 100 grams of a given tea was added to 800 ml of boiling water in a container. In this embodiment, a stainless steel container was utilized although other suitable containers may also be used. The container was then covered and boiled for 15 minutes with occasional stirring. The heat was turned off and the decoction was allowed to cool while covered on the burner. After approximately 8 hours, the cool tea decoction was filtered and aliquoted in 250 ml bottles. In the examples described herein, the decoction was filtered once through cheesecloth. This filtering step removes large particulate compounds from the decoction and as such it is to be understood that other methods for removing the large particulate compounds may also be used. Following filtration, the tea decoction contained small particulate matter.

As will be appreciated by one knowledgeable in the art, methods for preparing the decocted tea may vary, according to the brand and type of tea used. For example, the volume of water or weight of dried tea leaves may be varied The vanadate was then suspended in the tea. Specifically, the quantity of vanadate added in the examples described herein was 15, 20 or 25 milligrams/ml as described below. In the examples described herein, sodium orthovanadate from Sigma™ was used as the vanadate source. As will be apparent, other suitable forms of vanadate, for example, vanadyl sulfate or sodium metavanadate may also be used. The decocted tea plus vanadate was allowed to stand for 8 hours prior to use. It is of note that bottles were shaken prior to the removal of an aliquot for administration purposes.

As discussed below, vanadate suspended in either water, black tea or green tea at concentrations of 15, 20 or 25 mg/ml was administered to test animals in a 2 ml aliquot by oral gavage. In these experiments, the test animals were streptozotocin-induced diabetic rats. The animals were identified by number and by the presence or absence of a red stripe, designated Red and None respectively. As discussed in the accompanying tables, the dosage regime was different for each animal, depending upon their response to treatment. That is, some animals received only two to three doses of the vanadate/tea mixture and were normoglycemic for from three to six weeks without further doses. Other animals responded to treatment with the decocted tea and vanadate mixture but remained normoglycemic for only a few days, requiring more frequent doses. It is also of note that some test animals did not respond to treatment, while other developed vanadate-associated diarrhea and died, as described below. During the course of the study, body weight (FIGS. 2–4) and blood glucose levels (FIGS. 5–7) were also monitored at regular intervals, as described below. Specifically, blood glucose levels were measured using glucose test strips and a drop of blood obtained via the tail snip method, as known in the art.

The relevant data for each of the animals in the test groups are summarized in TABLEs 1–9.

Specifically, TABLE 1 summarizes the results observed using animals administered doses of 30 mg of vanadate suspended in water. As can be seen, two (37 Red and 38 None) of the six animals died of diarrhea, a common side effect of vanadate treatment, as discussed above. However, two of the animals (38 Red and 39 Red) required only two doses of the vanadate water mixture. As can be seen, in these animals, blood glucose levels remained normal approximately five weeks after the last dose. Furthermore, one animal (38 None) usually responded to vanadate treatment but blood glucose levels remained normal for only a few days, meaning that more frequent doses were needed. Finally, in animal 37 None, blood glucose level was difficult to control and remained elevated after the $7^{th}$ dose.

Referring to TABLE 2, it is of note that three (34 Red, 35 Red and 36 None) of the animals administered 40 mg doses of vanadate suspended in water died of diarrhea. However, one animal (36 Red) required only two doses of the vanadate water mixture to retain normal blood glucose levels approximately five weeks after the last dose. Furthermore, one animal (34 None) usually responded to vanadate but the blood glucose levels remained normal for only a few days, meaning that more frequent doses were needed. Finally, in animal 36 None, blood glucose level was difficult to control and remained elevated after the $6^{th}$ dose.

Referring to TABLE 3, it is of note that three (31 Red, 32 Red and 32 None) of the animals administered 50 mg doses of vanadate suspended in water died of diarrhea. Furthermore, one animal (33 None) required three doses of the vanadate water mixture to retain normal blood glucose levels approximately three weeks after the last dose. In addition, one animal (31 None) usually responded to vanadate but had blood glucose levels that remained normal for only about two days, meaning that more frequent doses were needed. Finally, one animal (33 Red) had blood glucose levels that were elevated after the final dose although this animal had previously responded to vanadate.

Figure 2:
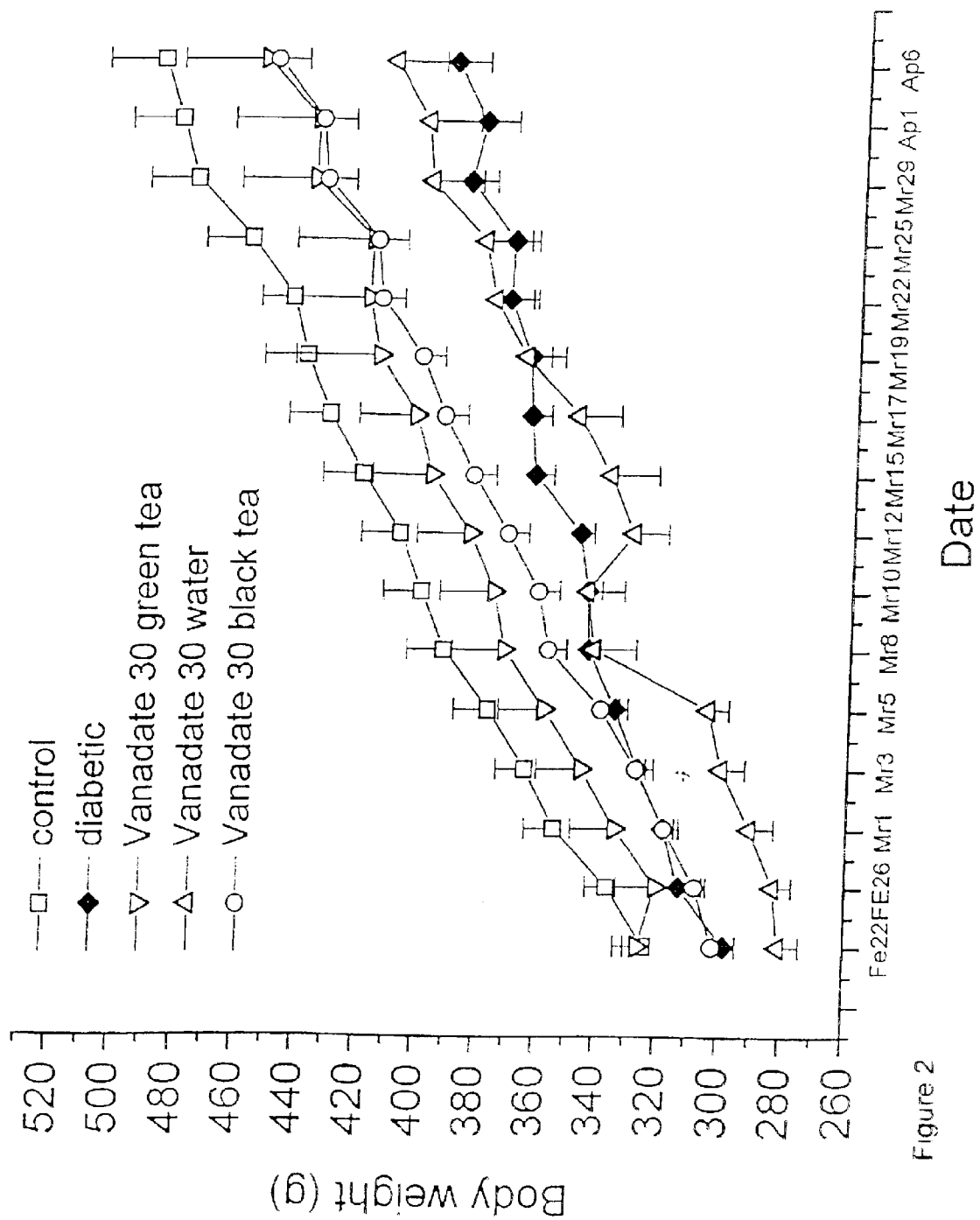
FIG. 2 is a graph of body weight over time of subjects administered 30 mg of vanadate suspended in green tea, black tea and water, as well as wild type and diabetic controls.
Figure 3:
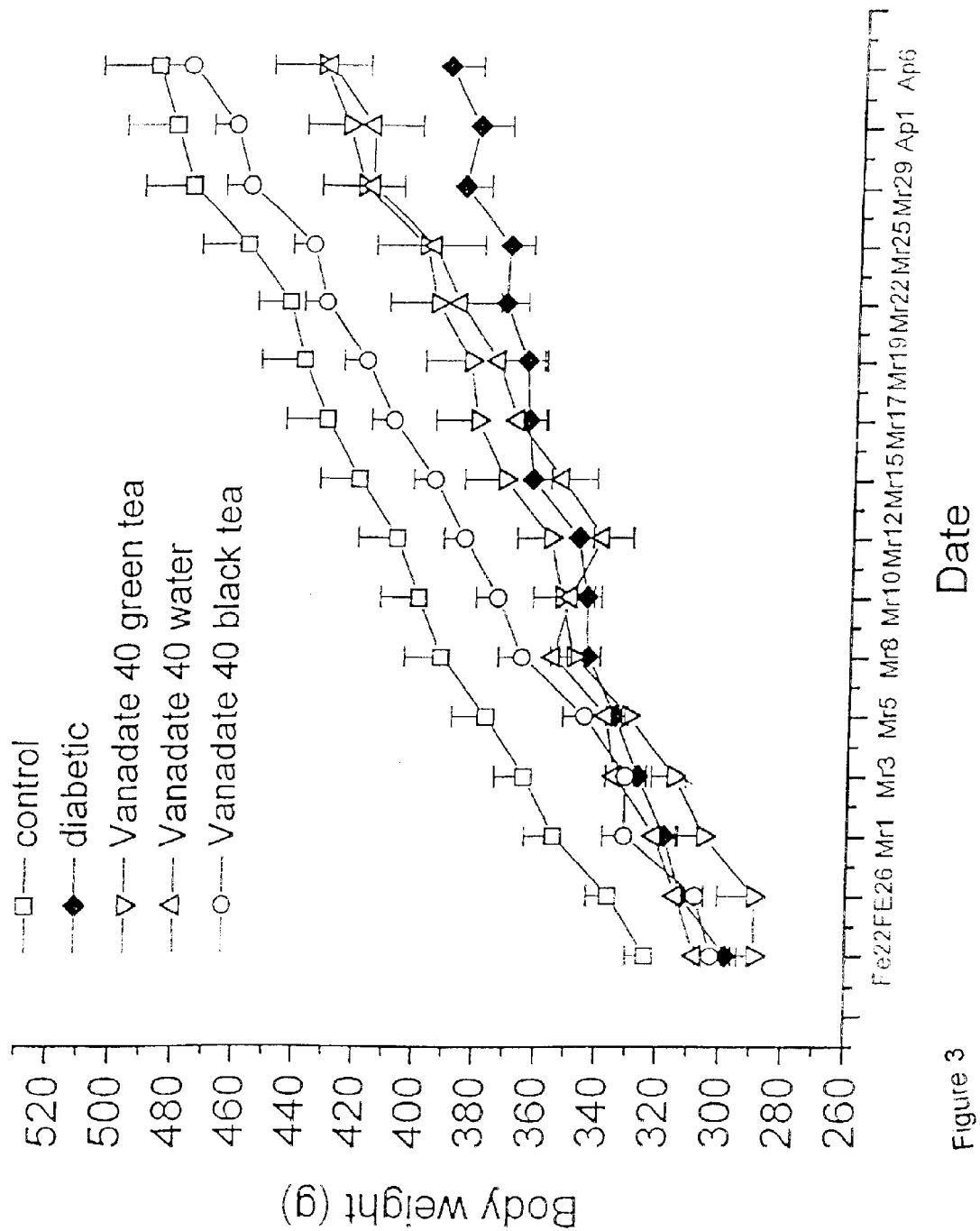
FIG. 3 is a graph of body weight over time of subjects administered 40 mg of vanadate suspended in green tea, black tea and water, as well as wild type and diabetic controls.
Figure 4:
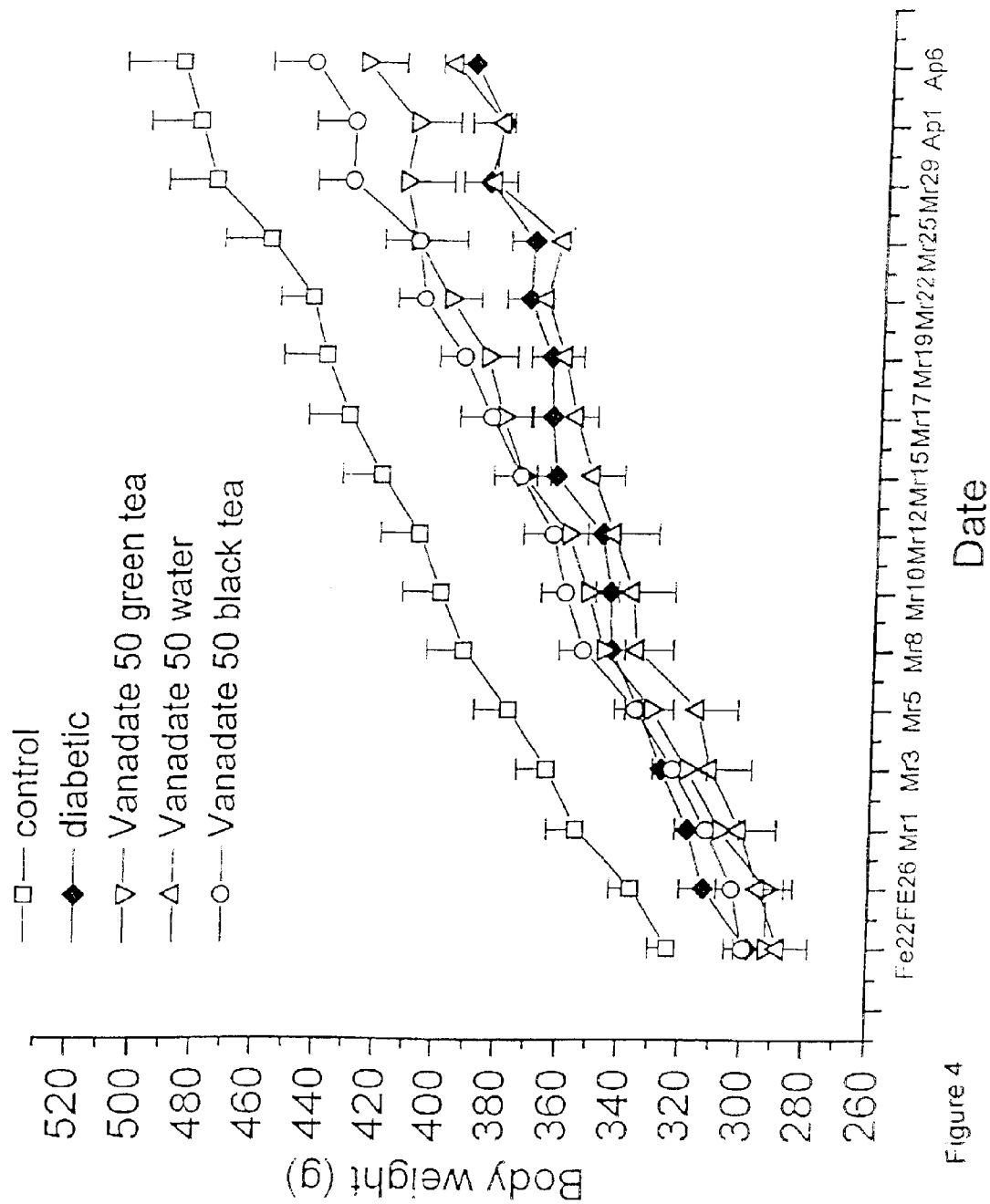
FIG. 4 is a graph of body weight over time of subjects administered 50 mg of vanadate suspended in green tea, black tea and water, as well as wild type and diabetic controls.

The results obtained indicate that the vanadate suspended in water produced somewhat variable results in terms of normalization of blood glucose levels and also side effects. Specifically, as shown in FIG. 1, the vanadate and water mixture caused considerable mortality. Furthermore, as shown in FIGS. 2–4, the water and vanadate mixture did not promote significant weight gain compared to the diabetic control.

Referring to TABLE 4, animals were administered doses of 30 mg vanadate suspended in decocted green tea. As can be seen, all four animals (13 Red, 13 None, 16 Red and 16 None) received multiple doses of the vanadate green tea mixture and their blood glucose level remained elevated.

Referring to TABLE 5, animals were administered 40 mg vanadate suspended in decocted green tea. As can be seen, one animal (10 None) died from diarrhea. Two others (10 Red and 12 Red) received multiple doses of the vanadate green tea mixture and their blood glucose level remained elevated. However, three animals (11 Red, 11 None and 12 None) received from two to three doses of the vanadate green tea mixture and retained normal blood glucose levels for 3–5 weeks after the final dose.

Referring to TABLE 6, animals were administered 50 mg vanadate suspended in decocted green tea. As can be seen, one animal (9 None) died from diarrhea. Three others (7 Red, 8 None and 9 Red) received multiple doses of the vanadate green tea mixture and their blood glucose level remained elevated. However, four animals (6 Red, 6 None, 7 None and 7 Red) received from two to three doses of the vanadate green tea mixture and retained normal blood glucose levels for 4–5 weeks after the final dose.

The results obtained with the vanadate and green tea mixtures indicate that higher concentrations of vanadate (50 mg) produced the desired results, that is, promoted normal blood glucose levels after only a few doses. Referring to FIG. 1, it can be seen that the vanadate and green tea mixture had a higher survival rate than the vanadate and water mixture. Furthermore, the vanadate and green tea mixture promoted weight gain at a rate higher than the diabetic control as shown in FIGS. 2–4. Thus, the vanadate and green tea mixture was more apt at managing blood glucose levels and also had fewer side effects compared to the vanadate and water mixture.

Referring to TABLE 7, animals were administered 30 mg doses of vanadate suspended in decocted black tea. As can be seen, two animals (48 Red and 48 None) required multiple doses and their blood glucose level remained difficult to control throughout the study. Furthermore, one animal (51 None) always responded to the vanadate doses but the blood glucose levels remained normal for only a few days, meaning that multiple treatments were required. However, six animals (47 Red, 49 Red, 49 None, 50 Red, 50 None and 50 Red) required only two doses and maintained normal glucose levels approximately five weeks after the final dosage.

Referring to TABLE 8, animals were administered 40 mg doses of vanadate suspended in decocted black tea. As can be seen, one animal (55 Red) died from diarrhea. However, nine animals (52 Red, 52 None, 53 Red, 53 None, 54 Red, 54 None, 55 None, 56 Red and 56 None) required only two to three doses of the vanadate black tea mixture and maintained normal blood glucose levels for three to five weeks after the last dose.

Referring to TABLE 9, animals were administered 50 mg doses of vanadate suspended in decocted black tea. As can be seen, three animals (44 None, 41 None and 40 None) died from diarrhea. Two others (41 Red and 44 Red) were usually responsive to vanadate but blood glucose levels increased after only a few days, necessitating several doses. However, five animals (40 Red, 42 Red, 42 None, 43 Red and 43 None) required only two to three doses of the vanadate black tea mixture and maintained normal blood glucose levels for three to five weeks after the last dose.

Thus, the mixture of vanadate and black tea produced the desired results at the low and medium vanadate concentrations (30 mg and 40 mg). That is, these doses stabilized blood glucose levels after only a few doses. Furthermore, there is considerably less variability in the results obtained compared to the water and vanadate mixture. Finally, the vanadate and black tea mixture had a low mortality rate as shown in FIG. 1 and increased weight gain, as shown in FIGS. 2–4.

The above-described results are summarized in the figures.

Specifically, FIG. 1 plots survival against vanadate dosage. As can be seen, suspension of the vanadate in either decocted black tea or decocted green tea results in increased survival compared with similar quantities of vanadate suspended in water. This clearly shows that the suspension of the vanadate in the decocted tea helps to overcome the side effects associated with vanadate administration.

FIGS. 2–4 show weight gain over time of animals administered varying doses of vanadate suspended in water, decocted black tea or green tea. As can be seen, animals administered vanadate suspended in water tended to gain weight at a rate very similar to the diabetic control. However, animals administered vanadate suspended in decocted black tea or decocted green tea tended to gain weight at a rate more similar to that of wild type animals. As can be seen, the plot of 30 mg (FIG. 2) and particularly 40 mg (FIG. 3) vanadate resuspended in black tea closely follows that of wild type.

Figure 5:
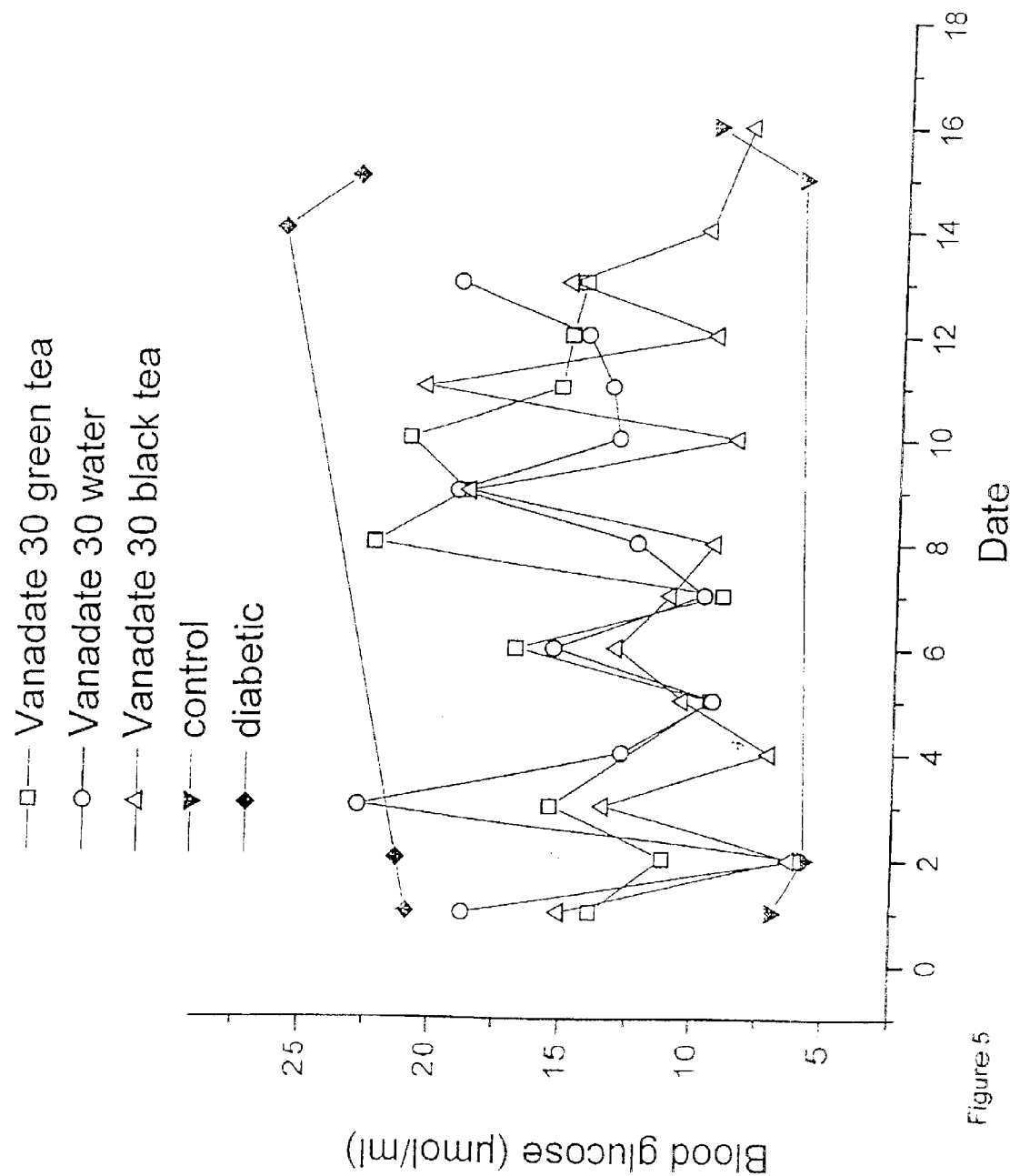
FIG. 5 is a plot of blood glucose levels over time in subjects administered 30 mg of vanadate suspended in green tea, black tea and water, as well as wild type and diabetic controls.
Figure 6:
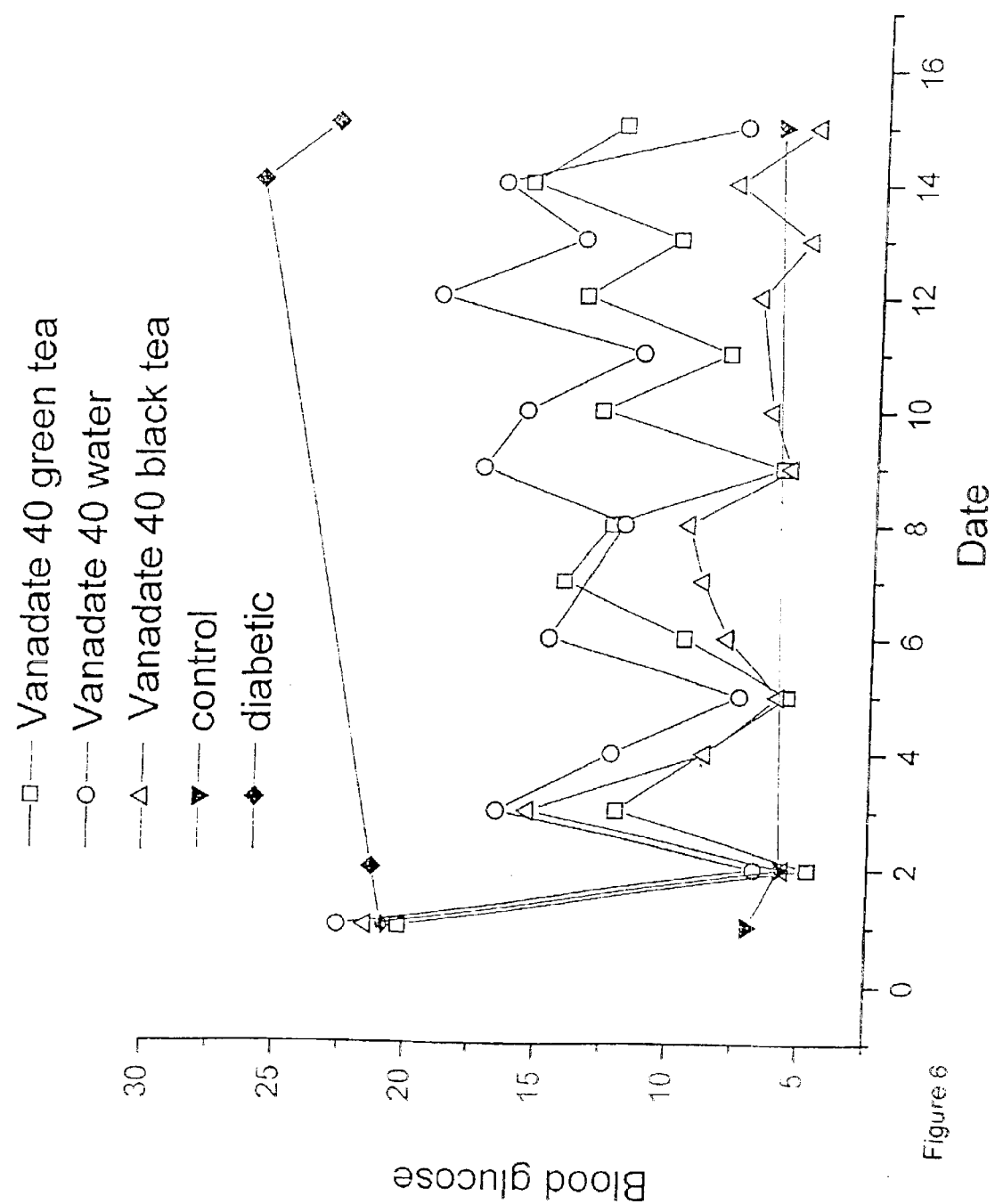
FIG. 6 is a plot of blood glucose levels over time in subjects administered 40 mg of vanadate suspended in green tea, black tea and water, as well as wild type and diabetic controls.
Figure 7:
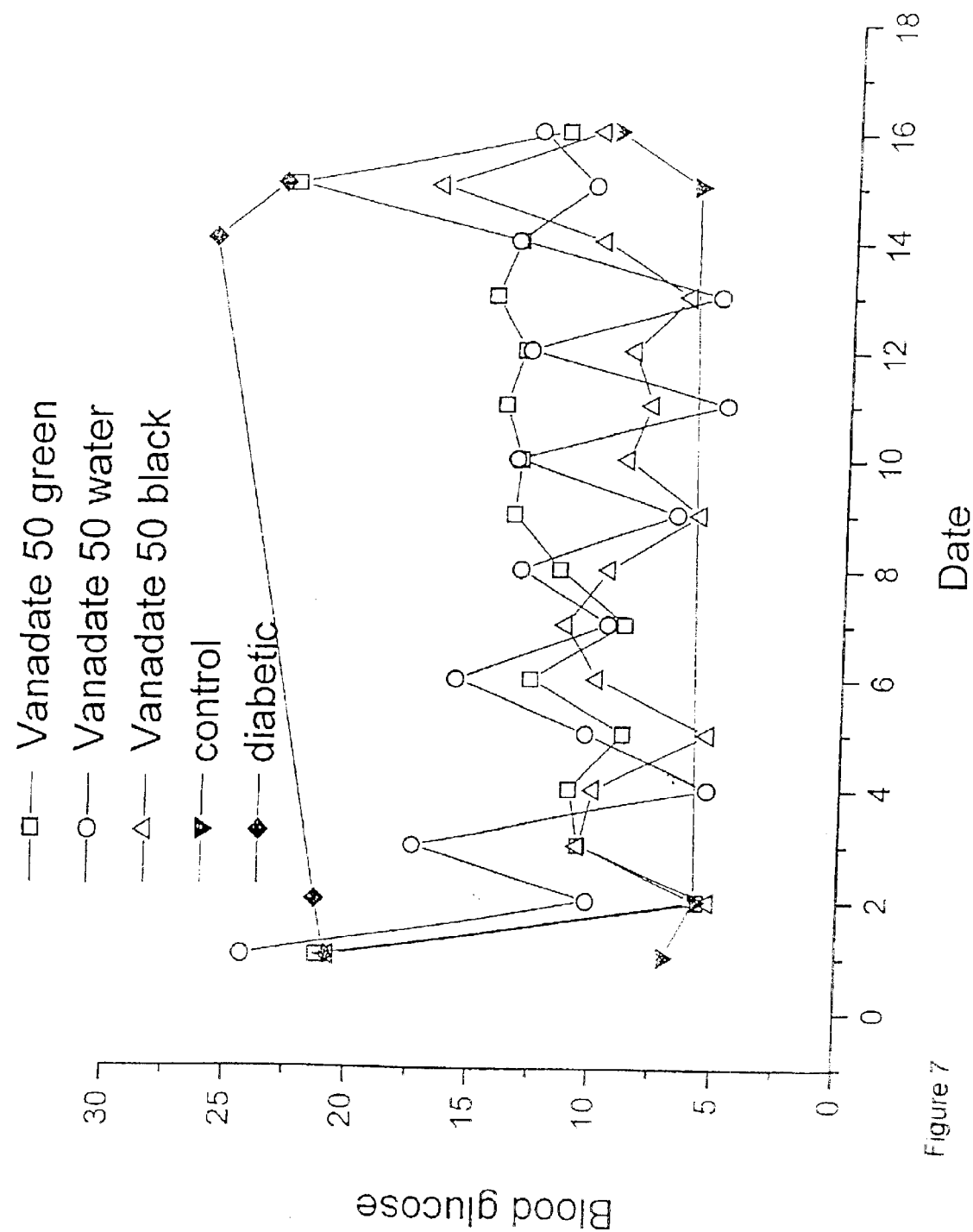
FIG. 7 is a plot of blood glucose levels over time in subjects administered 50 mg of vanadate suspended in green tea, black tea and water, as well as wild type and diabetic controls.

FIGS. 5–7 show blood glucose levels over time of animals administered varying doses of vanadate suspended in water, decocted black tea or green tea. As can be seen, the doses of vanadate, regardless of the carrier, caused blood glucose levels to decrease to approach normal levels. However, doses of 40 mg or 50 mg vanadate suspended in decocted tea caused blood glucose levels to remain relatively constant at near wild type levels.

Figure 12:
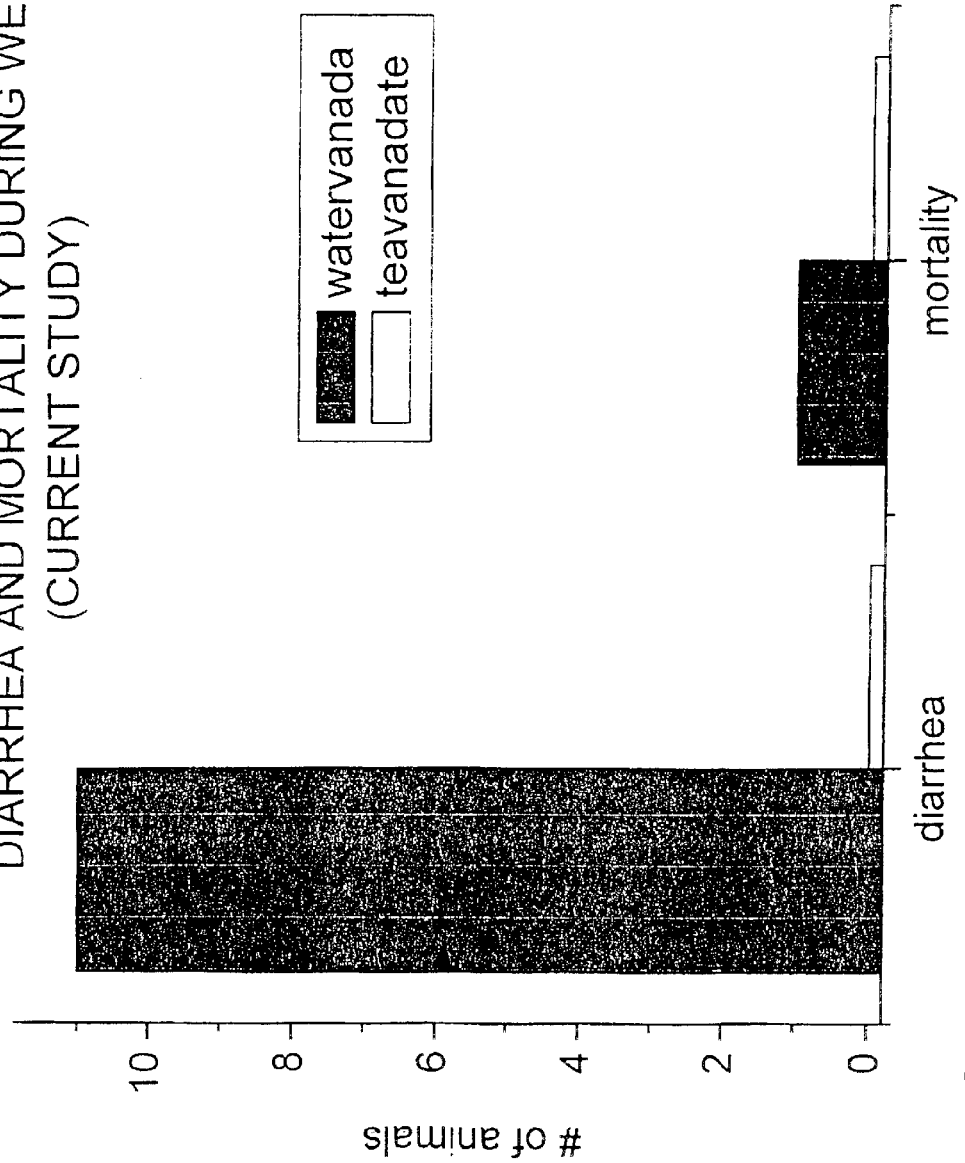
FIG. 12 shows the effects of sodium orthovanadate and black tea on the generation of diarrhea and death compared to vanadate delivered with water in streptozotocin-induced diabetic rats.

Sodium orthovanadate suspended in decocted black tea and vanadate suspended in water were administered separately to two groups of 14 streptozotocin-induced diabetic rats. Specifically, the administered dose was 40 mg vanadate per 2 ml. As can be seen in FIG. 12, 11 of the 14 rats administered vanadate in water developed diarrhea and 1 of the 14 rats died. Conversely, none of the rats administered sodium orthovanadate in decocted black tea developed diarrhea.

Figure 13:
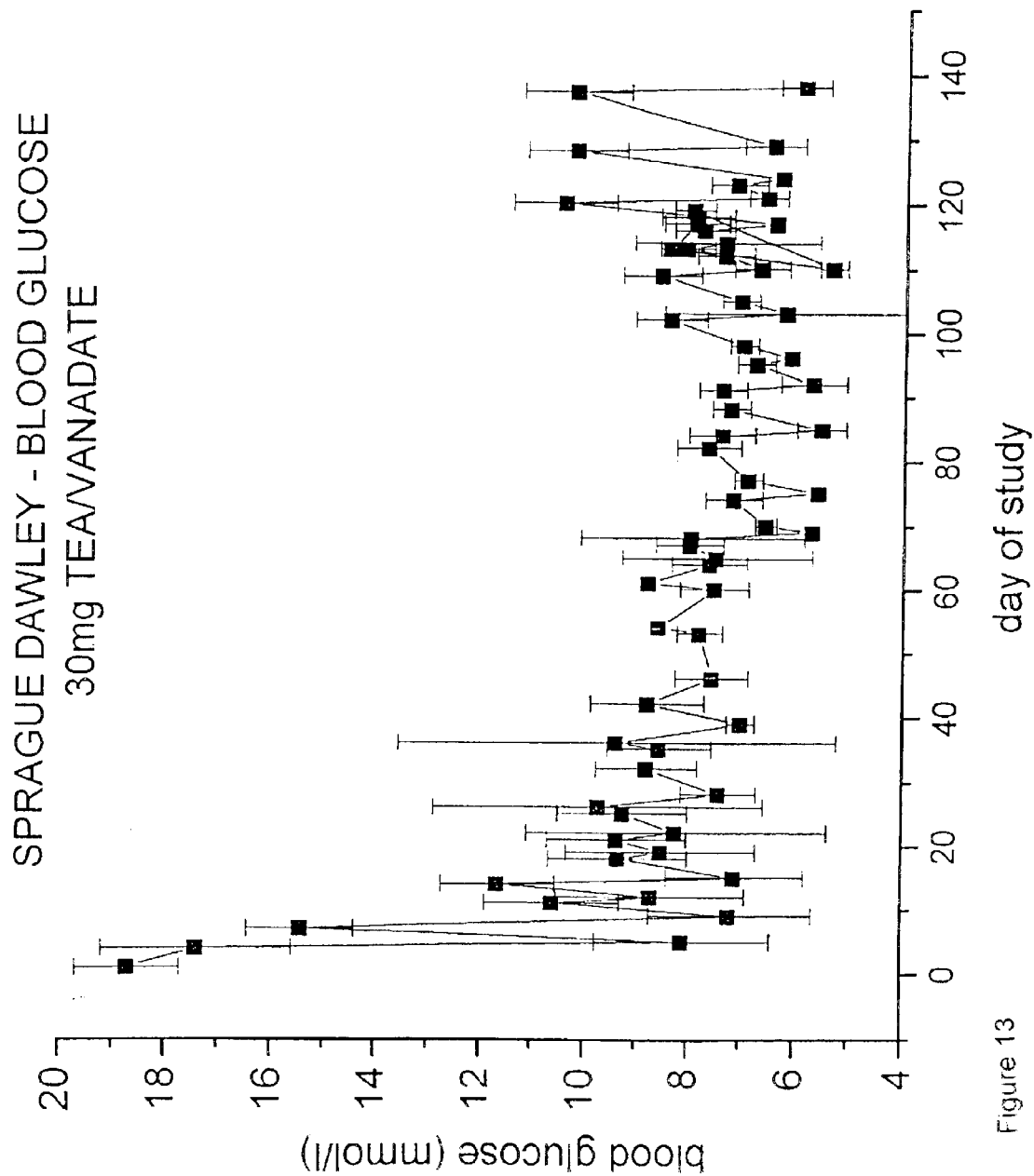
FIG. 13 shows the effect of sodium orthovanadate and black tea on blood glucose concentration in streptozotocin-induced diabetic rats.

Sodium orthovanadate suspended in decocted black tea was administered to 14 streptozotocin-induced diabetic rats at a dosage of 30 mg per 2 mls. As can be seen in FIG. 13, this treatment reduced blood glucose to normal levels (<10 mmol/l) over extended periods of time.

Figure 14:
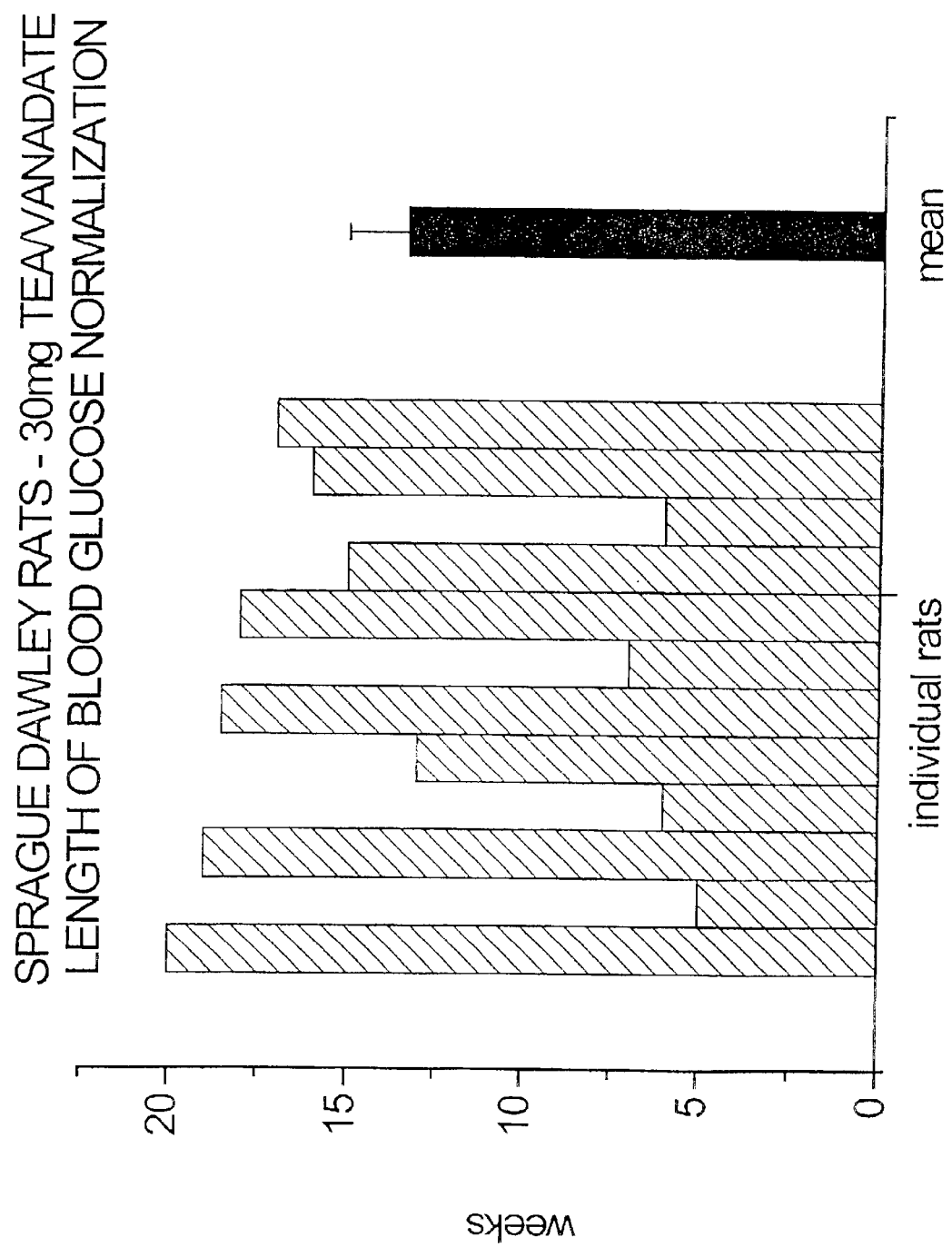
FIG. 14 shows the effect of sodium orthovanadate and black tea on individual blood glucose concentration in streptozotocin-induced diabetic rats.

Sodium orthovanadate suspended in decocted black tea was administered to 12 streptozotocin-induced diabetic rats at a dosage of 30 mg vanadate per 2 mls. Specifically, the rats were given 4–18 doses of the vanadate/tea mixture and thereafter remained untreated. FIG. 14 shows the number of weeks for which each of the 12 rats maintained normal blood glucose levels without further treatment. As can be seen, the length of time that blood glucose levels remained normal without further treatment varied from 5 weeks to 20 weeks in the rats, with a mean of 12 weeks.

Figure 15:
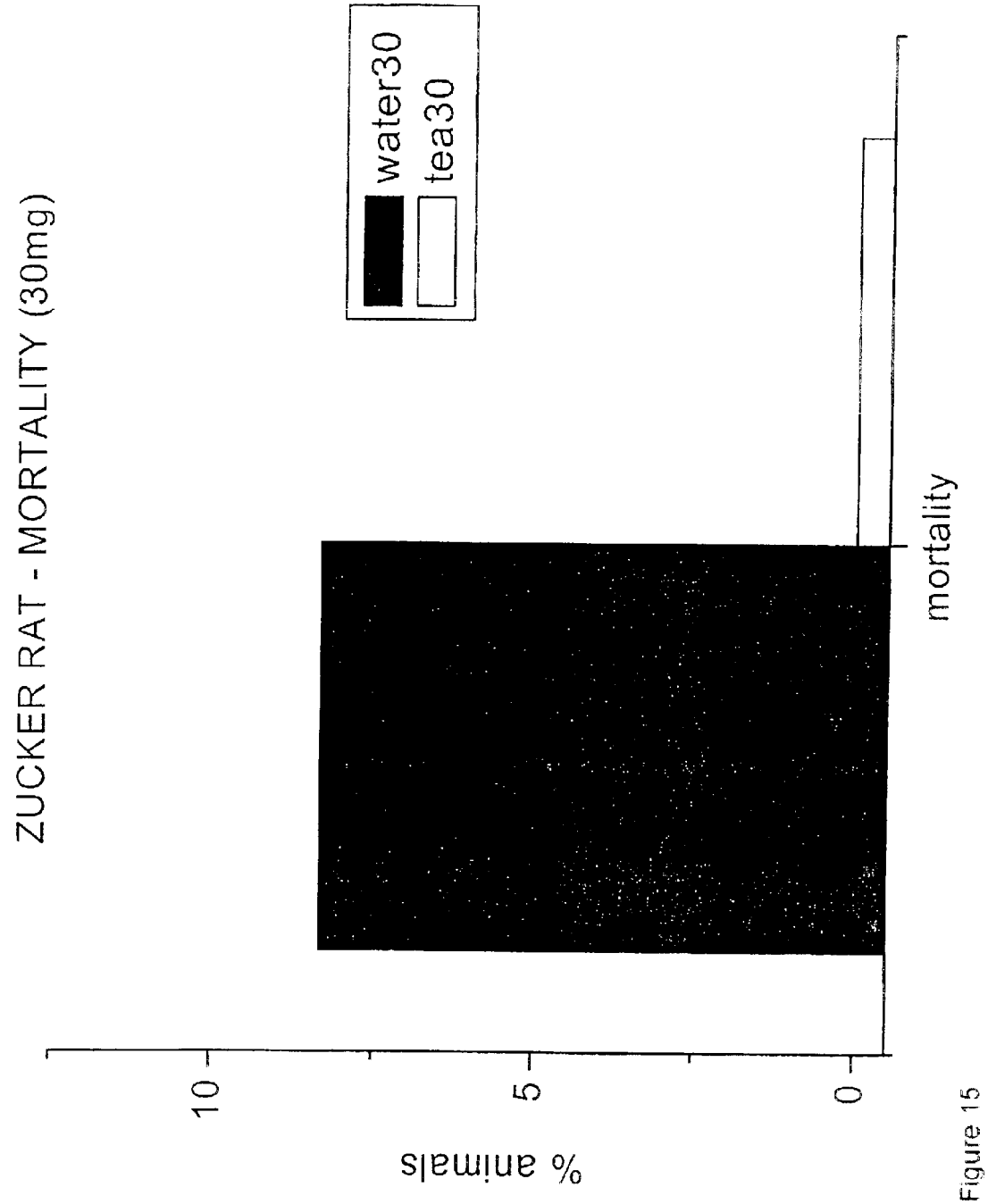
FIG. 15 shows the effect of sodium orthovanadate and black tea on mortality compared to vanadate delivered with water in Zucker diabetic rats.
Figure 16:
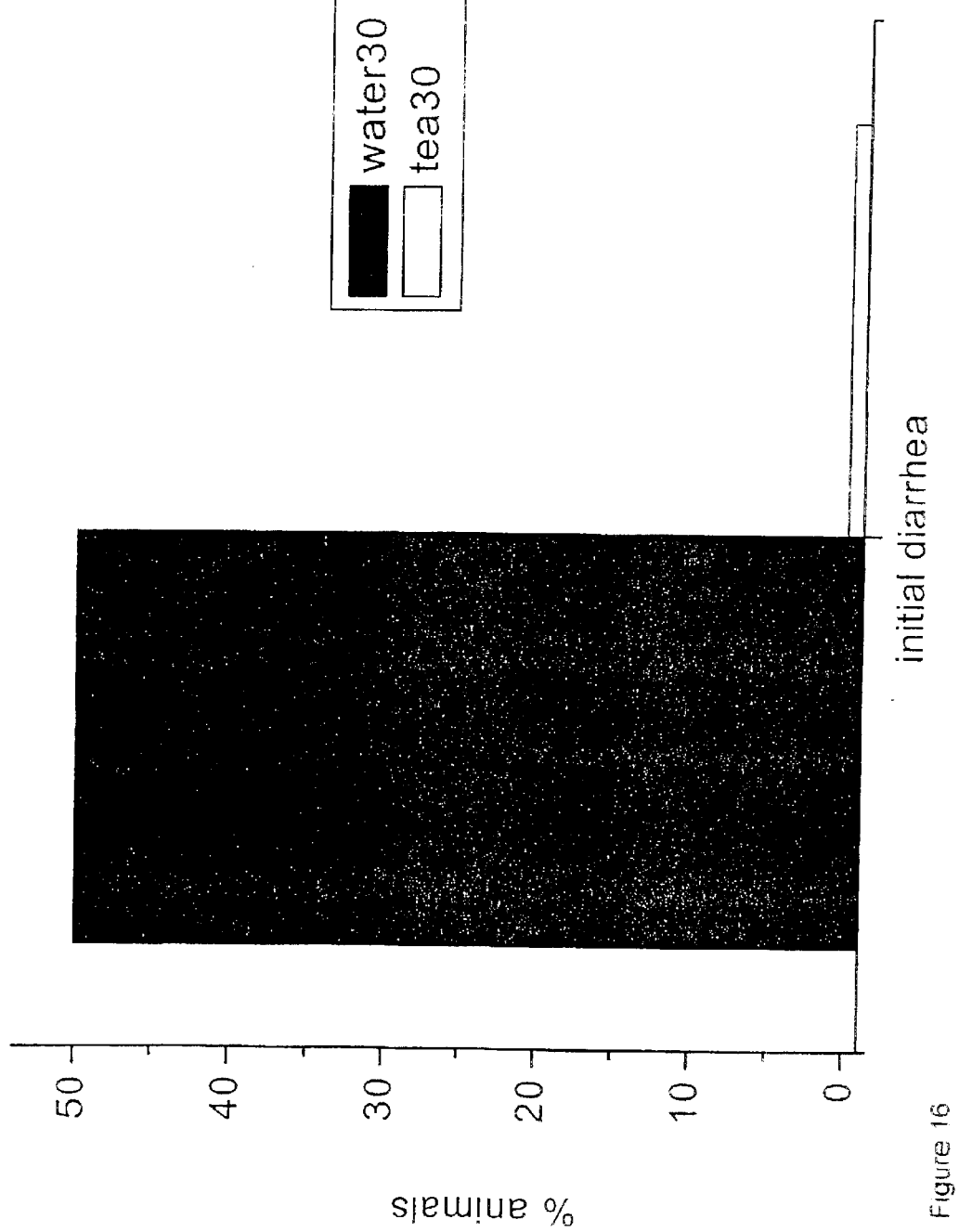
FIG. 16 shows the effect of sodium orthovanadate in black tea on diarrhea compared to vanadate delivered with water in Zucker diabetic rats.

Sodium orthovanadate suspended in decocted black tea and vanadate suspended in water were administered to individual test groups of Zucker diabetic rats at a dosage of 30 mg vanadate per 2 mls in both groups. As can be seen in FIG. 15, 8% mortality was seen in the group administered the vanadate/water mixture compared to 0% mortality in the group administered the black tea/vanadate mixture. Furthermore, as can be seen in FIG. 16, 50% of the water/vanadate test group developed diarrhea whereas none of the black tea/vanadate test group developed diarrhea.

The results clearly demonstrate that the diarrhea induced by vanadate when delivered in water is reduced or prevented when decocted tea is used as the delivery vehicle. Also, the animals gain weight during the treatment with vanadate suspended in decocted tea. Furthermore, and most importantly, delivery of the vanadate in the presence of decocted tea controls the blood sugar levels in diabetic rats for extended periods of time (>1 week). Clearly, this is superior to daily injections of insulin or daily doses of sulfonylurea drugs. The tea, therefore, prevents the diarrhea, maintains appetite and body weight and enhances the hypoglycemic action of vanadate.

Figure 8:
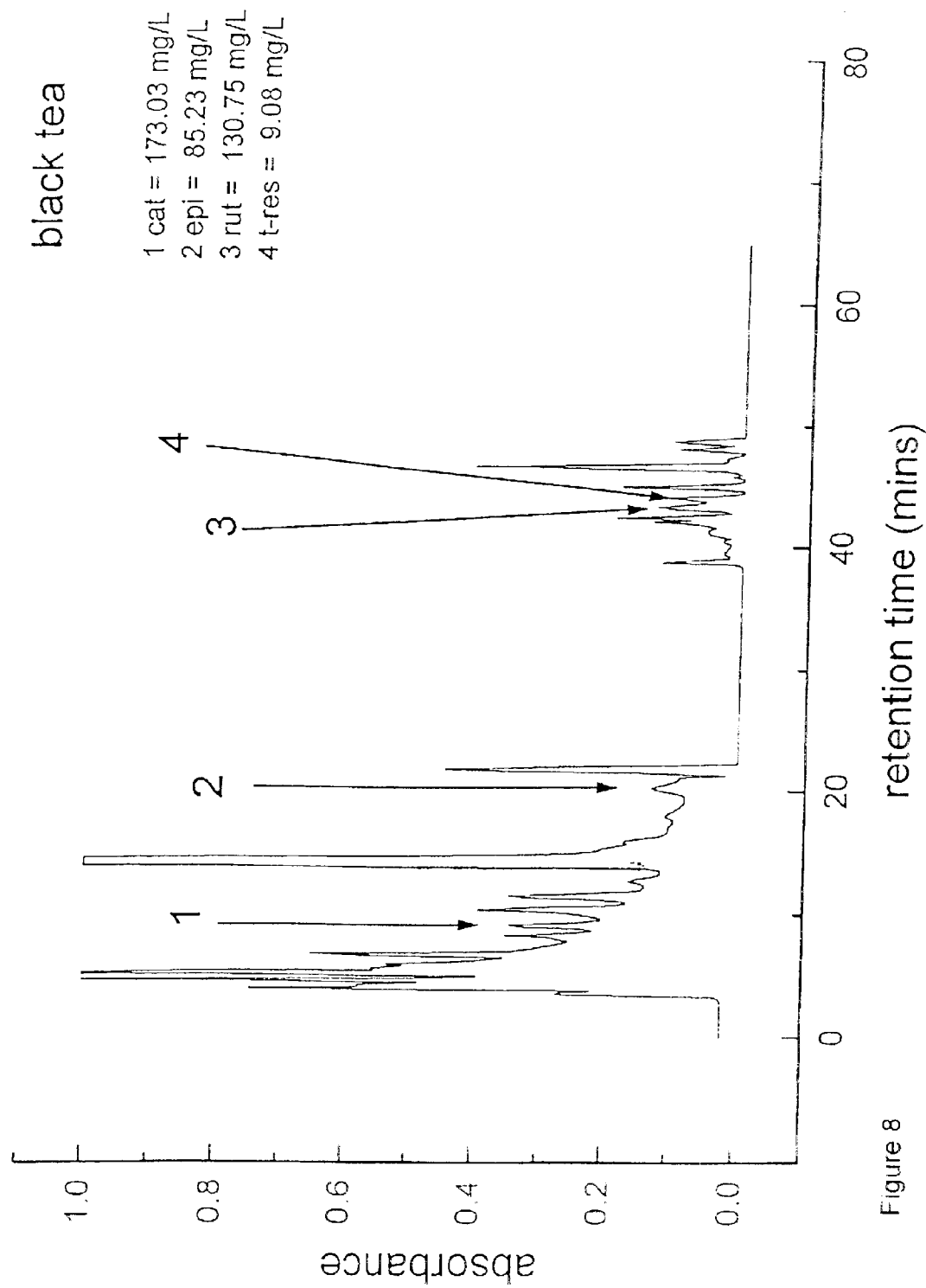
FIG. 8 shows a high performance liquid chromatographic separation of black tea, showing levels of antioxidants catechin (cat), epicatechin (epi), rutin (rut), transresveratrol (t-res) and quercetin (quer).
Figure 9:
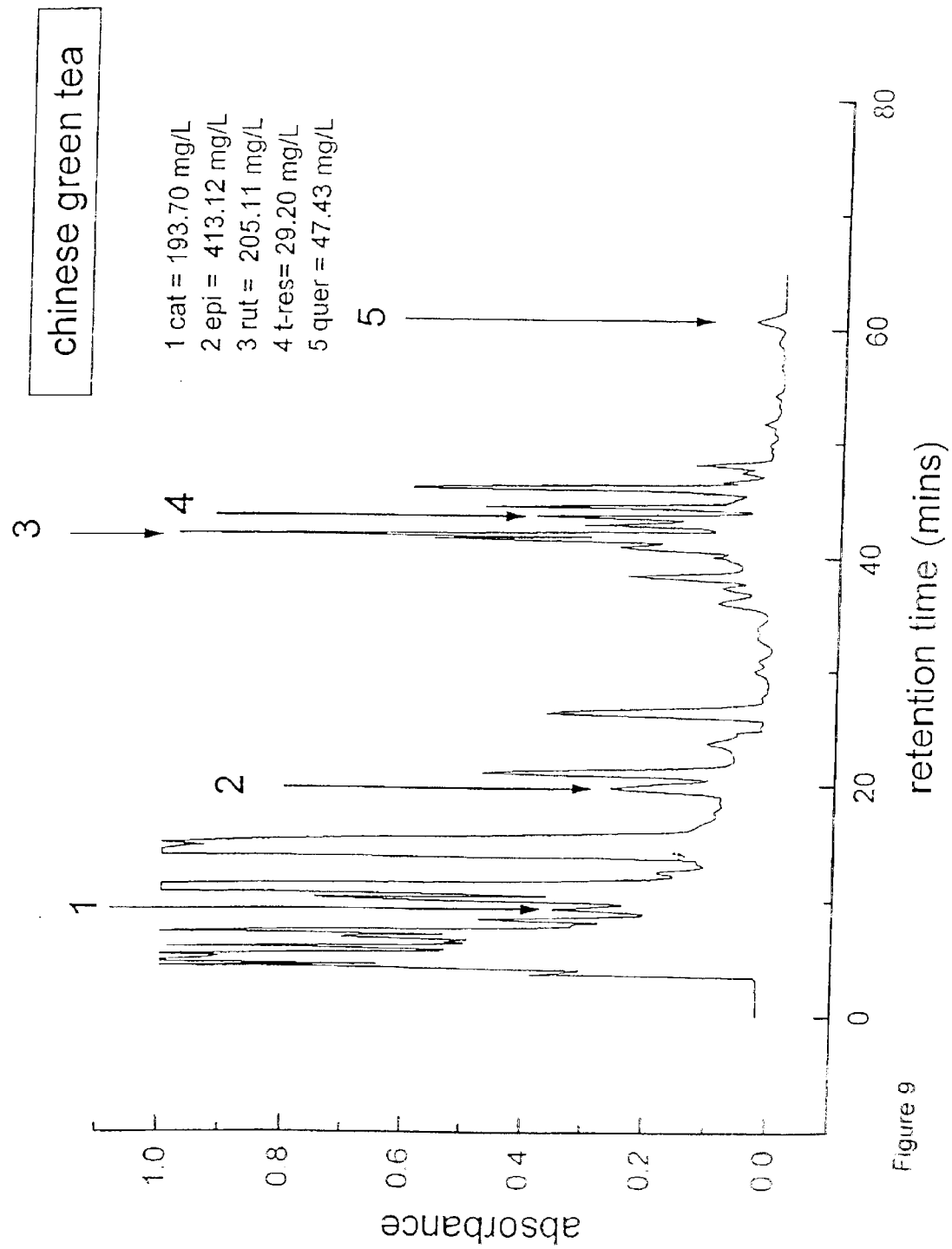
FIG. 9 shows a high performance liquid chromatographic separation of Chinese green tea, showing levels of antioxidants catechin (cat), epicatechin (epi), rutin (rut), transresveratrol (t-res) and quercetin (quer).
Figure 10:
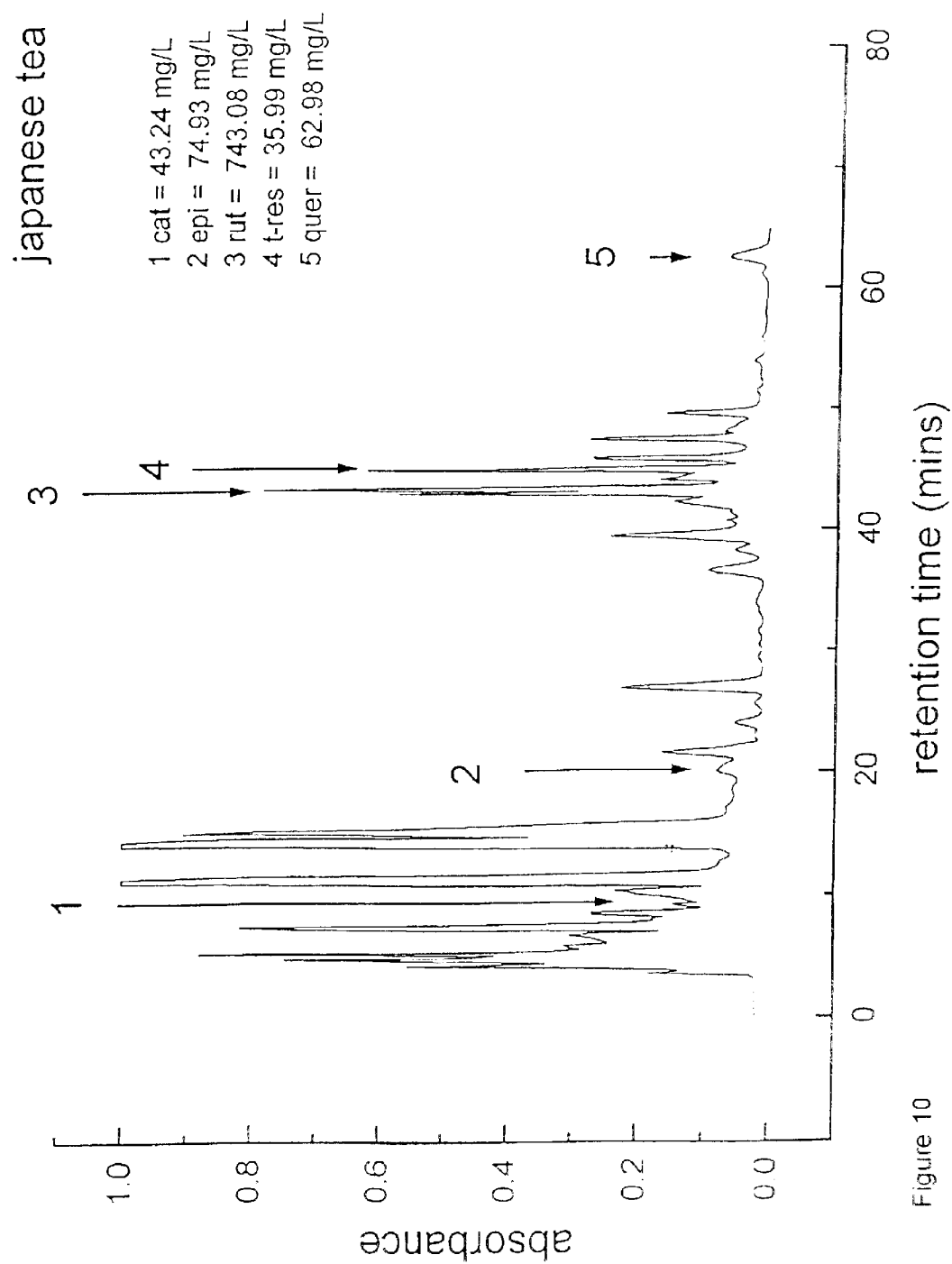
FIG. 10 shows a high performance liquid chromatographic separation of Japanese tea, showing levels of antioxidants catechin (cat), epicatechin (epi), rutin (rut), transresveratrol (t-res) and quercetin (quer).
Figure 11:
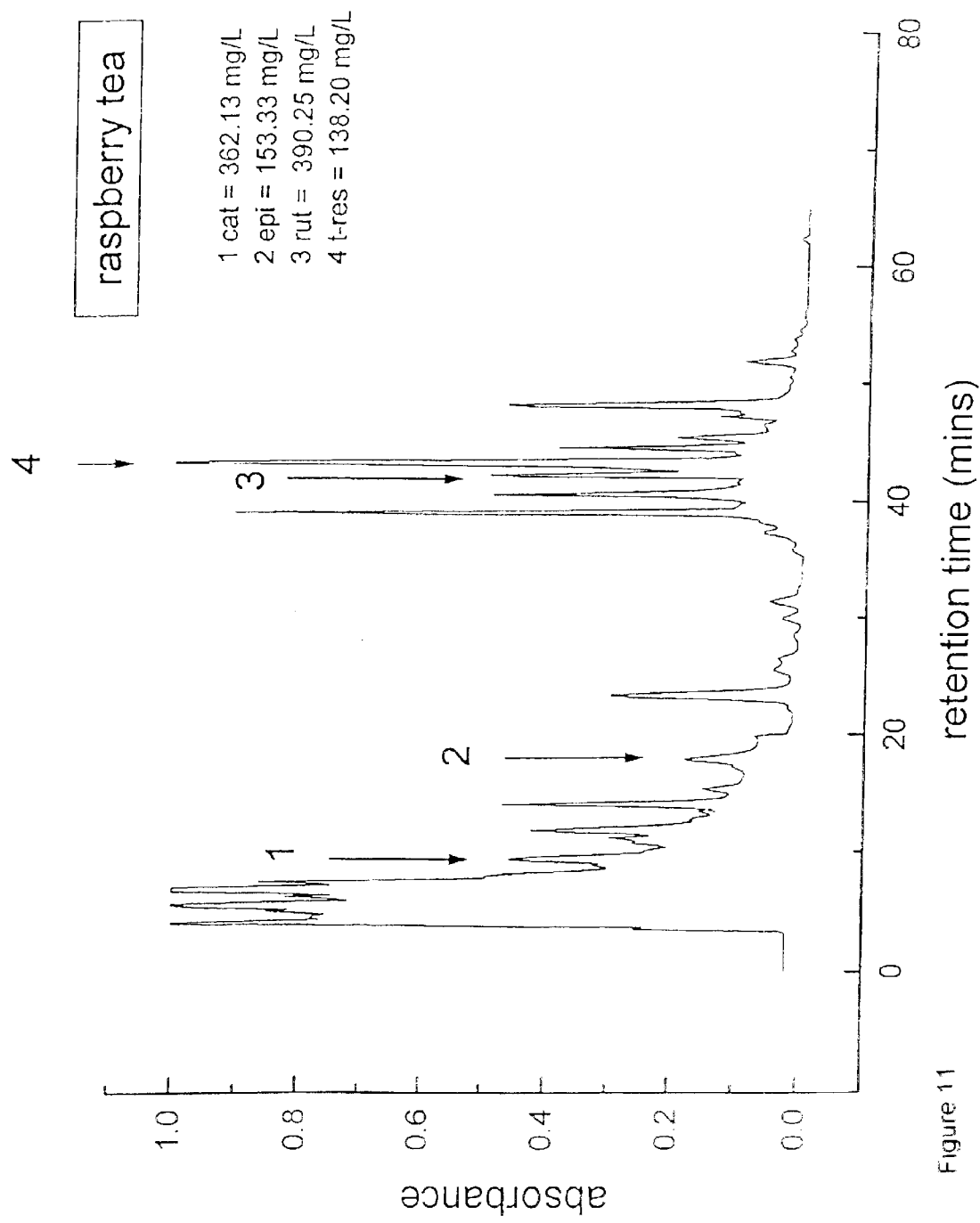
FIG. 11 shows a high performance liquid chromatographic separation of raspberry tea, showing levels of antioxidants catechin (cat), epicatechin (epi), rutin (rut), transresveratrol (t-res) and quercetin (quer).

Furthermore, it is of note that the effectiveness of the different concentrations of vanadate appeared to vary according to the specific tea used. That is, 40 mg of vanadate was most effective when suspended in decocted black tea, whereas 50 mg of vanadate was most effective when suspended in decocted green. This indicates that components of the teas are having an effect on the vanadate. As a result, high performance liquid chromatographic separation was carried out on the components within black tea (FIG. 8), Chinese green tea (FIG. 9), Japanese green tea (FIG. 10) and raspberry tea (FIG. 11). Five antioxidant peaks are identified: catechin (cat), epicatechin (epi), rutin (rut), transresveratrol (t-res) and quercetin (quer). Identified peaks were quantified with known standards.

In other experiments, sodium orthovanadate was suspended in decocted black tea or jasmine tea and the mixture was lyophilized. Specifically, in some experiments, 2.125 g of sodium orthovanadate was suspended in 600 ml of decocted black tea or jasmine tea, prepared as described above. The tea/vanadate solution was then placed in the freezer and frozen at −20° C. for approximately 72 hours. The frozen mixture was then placed in a Labconco™ lyophilizer for approximately 72 hours. The resulting powders were weighed and amounted to 5.1 g of black tea/vanadate and 4.5 g of jasmine tea/vanadate. To achieve an effective concentration of 40 mg vanadate/2 ml decocted tea for use in gavaging the diabetic rats, we calculated that 96 mg and 85 mg of the vanadate/black tea and vanadate/jasmine tea powders respectively were to be suspended in 2 ml of deionized water. The lyophilized powder dissolved in the water extremely quickly (within seconds).

Figure 17:
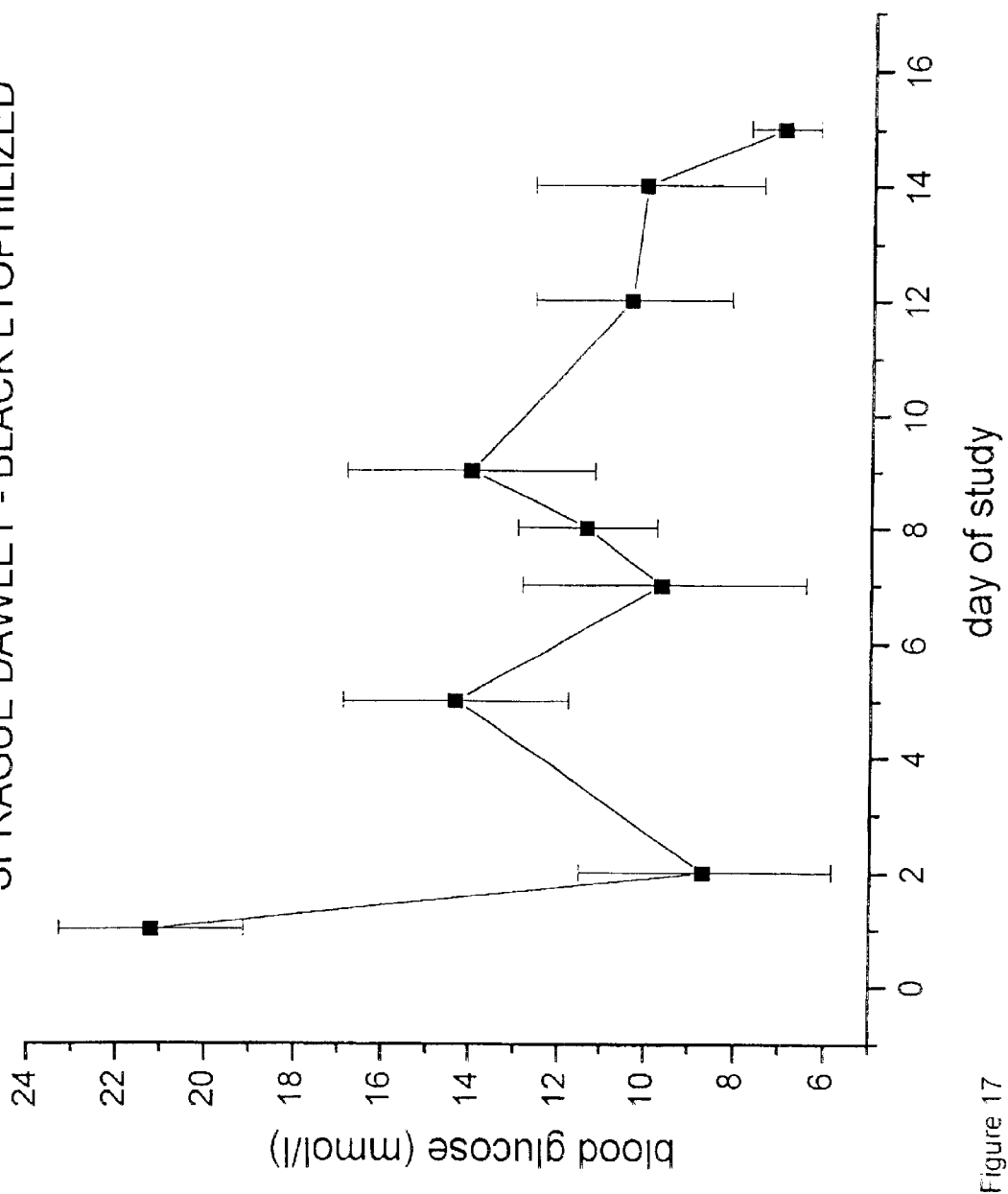
FIG. 17 shows the effect of lyophilized sodium orthovanadate in black tea on blood glucose levels in streptozotocin-induced diabetic rats.

Lyophilized black tea/vanadate was prepared as described above to a dosage of 40 mg per 2 mls. The mixture was administered to streptozotocin-induced diabetic rats and blood glucose levels were measured over time. As can be seen in FIG. 17, blood glucose levels dropped to normal levels, indicating that the lyophilization did not alter effectiveness.

Figure 18:
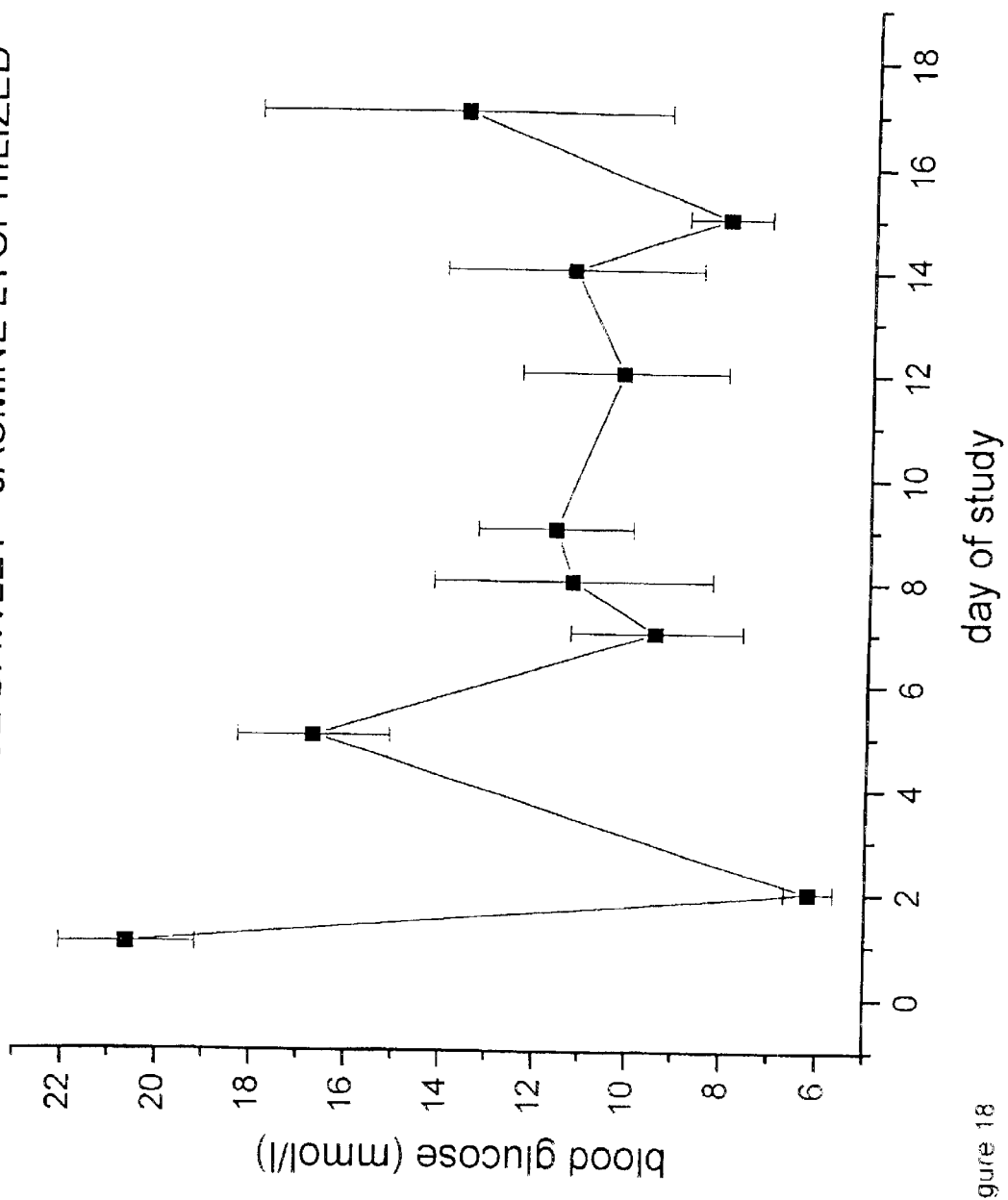
FIG. 18 shows the effect of lyophilized sodium orthovanadate in jasmine tea on blood glucose levels in streptozotocin-induced diabetic rats.

Lyophilized jasmine tea/vanadate was prepared as described above to a dosage of 40 mg per 2 mls. The mixture was administered to streptozotocin-induced diabetic rats and blood glucose levels were measured over time. As can be seen in FIG. 18, blood glucose levels dropped to normal levels, indicating that, as with the vanadate/black tea mixture, the lyophilization did not alter effectiveness. From this, it is evident that other known gastro-intestinal soothing teas may be utilized in the lyophilization process.

Figure 19:
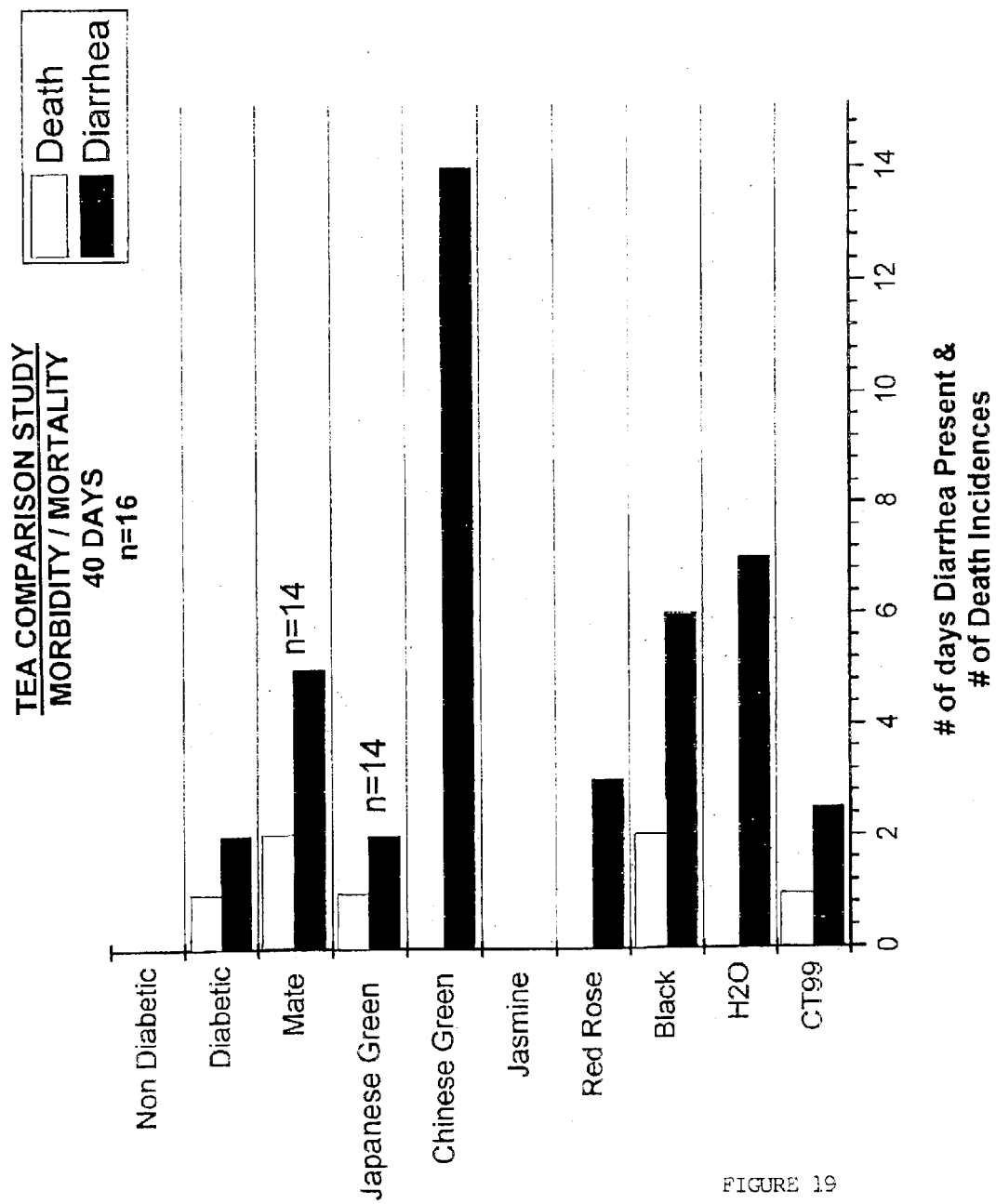
FIG. 19 shows a summary of the effect of vanadate suspended in a variety of teas on mortality and gastrointestinal distress.

As can be seen in FIG. 19, some of the teas tested, for example, Chinese green tea, caused considerable diarrhea and is therefore a poor choice for use in a pharmaceutical composition.

Figure 20:
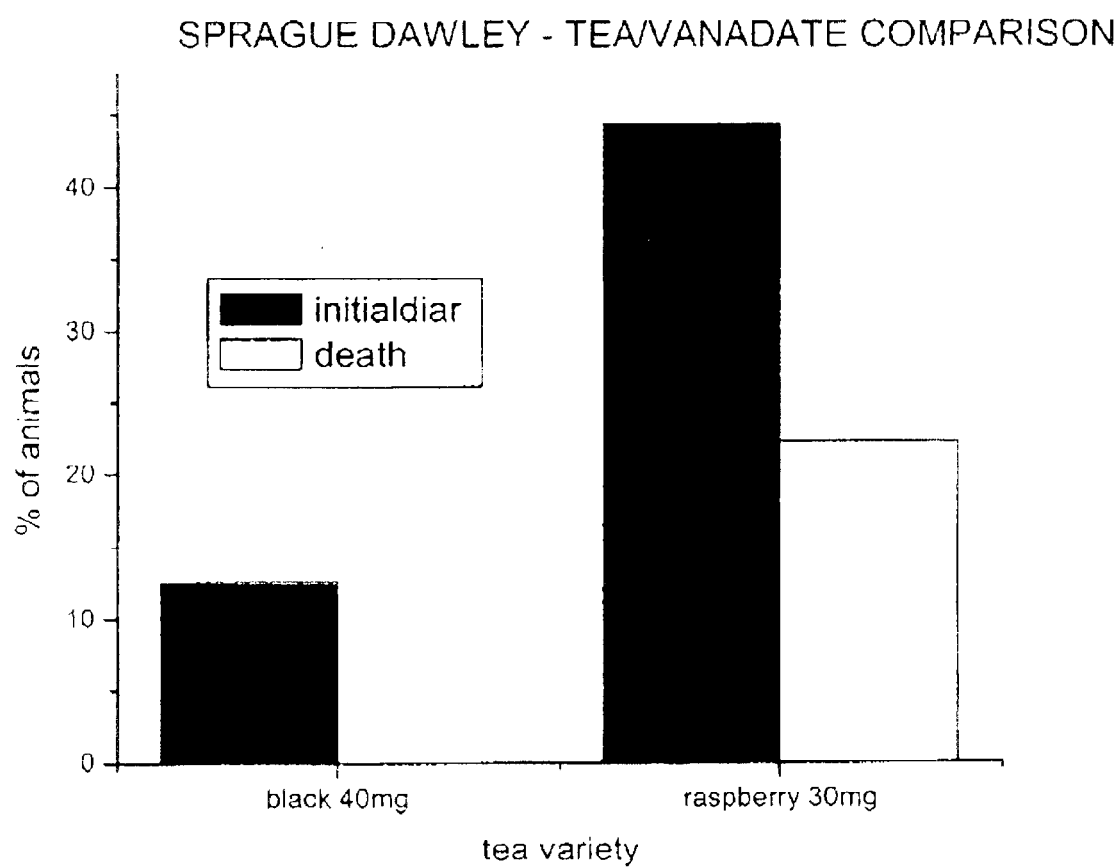
FIG. 20 compares the percentage of death and diarrhea from vanadate in black tea or raspberry tea.
Figure 21:
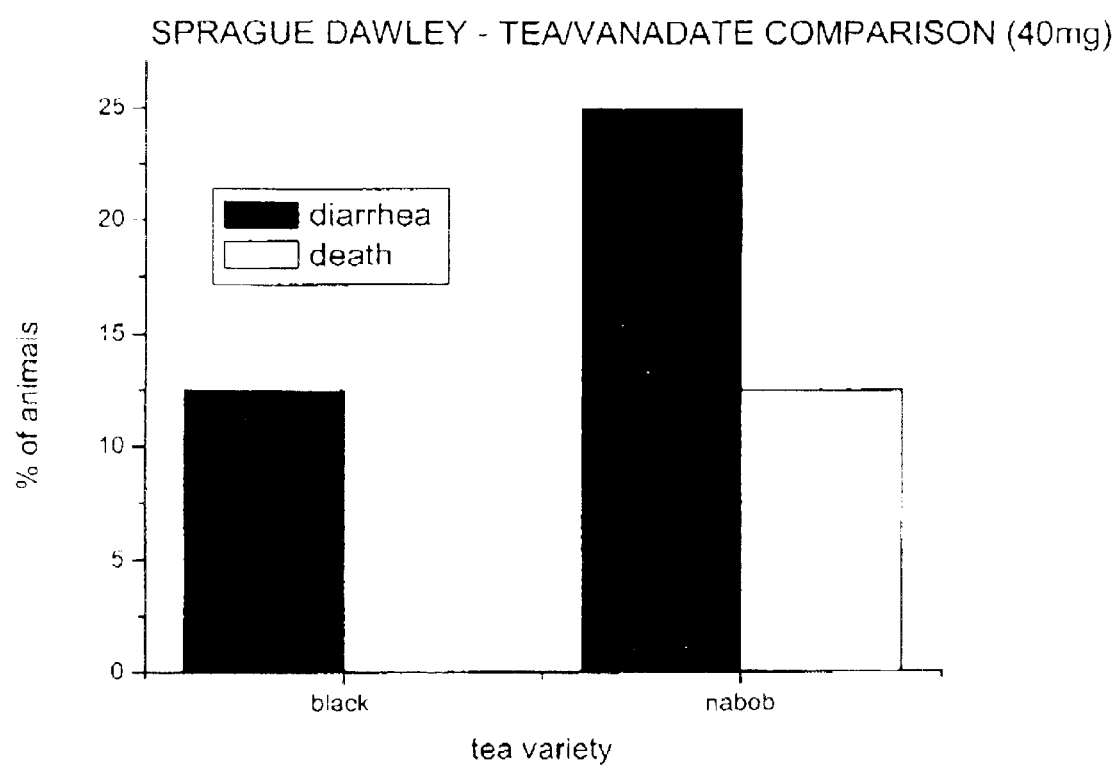
FIG. 21 compares the percentage of death and diarrhea from vanadate in black tea or NABOB™ tea.
Figure 22:
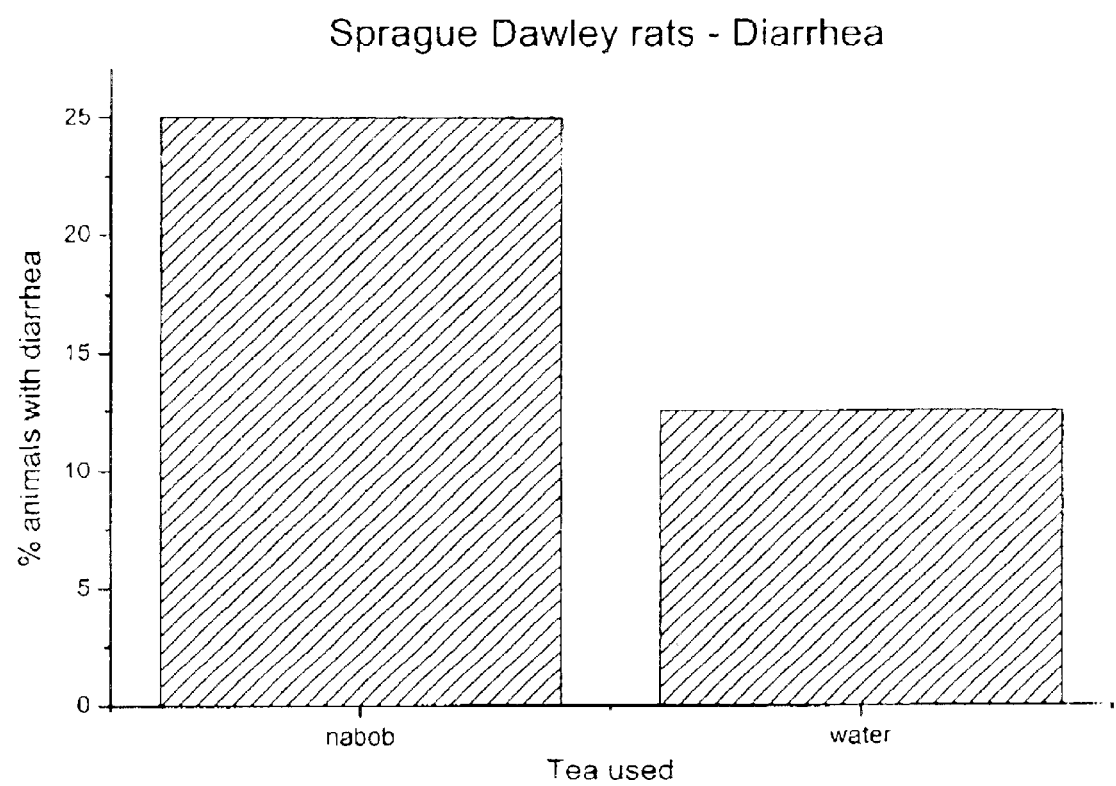
FIG. 22 compares the percentage of diarrhea from vanadate in NABOB™ tea or water.
Figure 23:
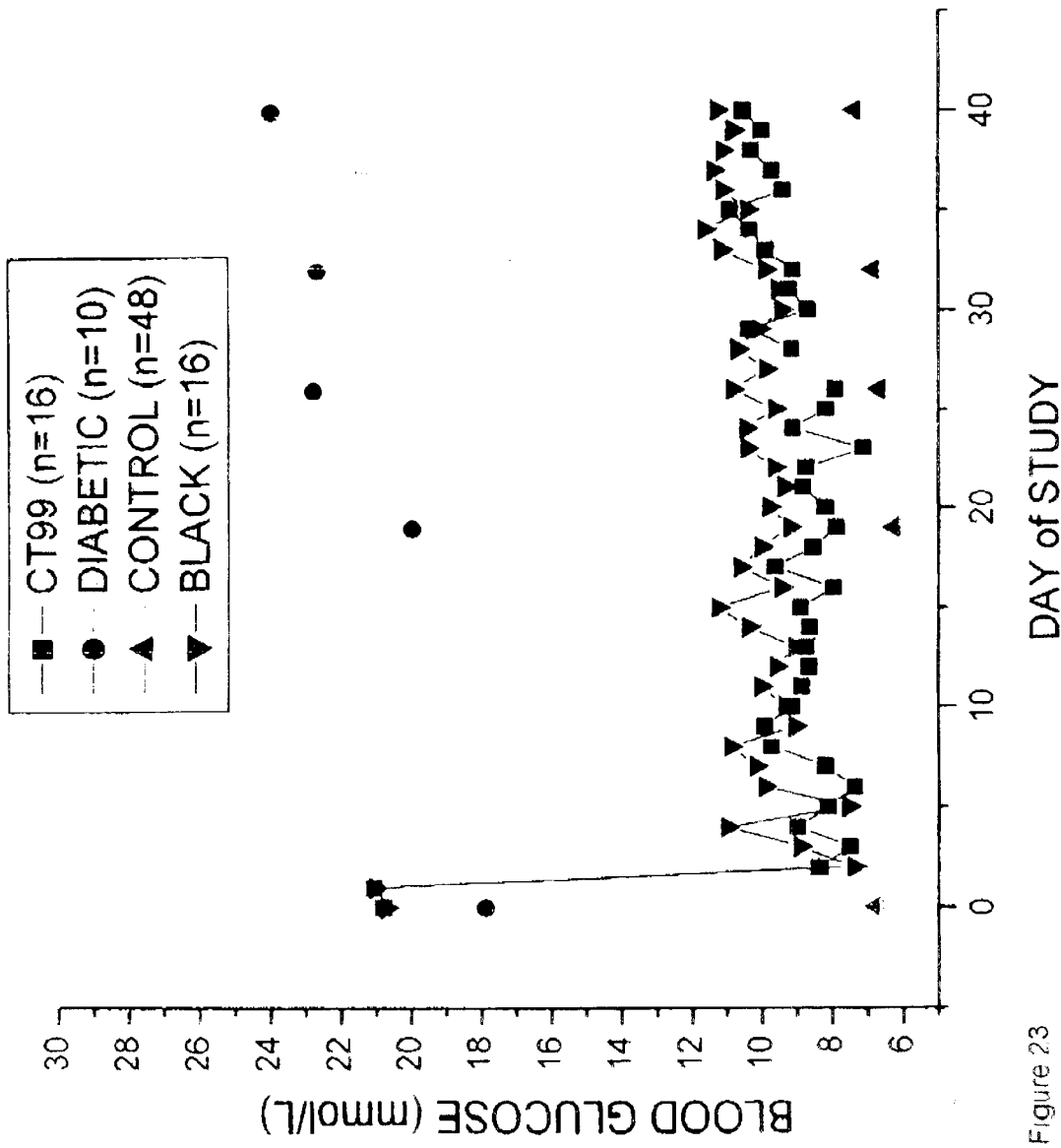
FIG. 23 compares blood glucose levels over time when administered lyophilized vanadate in tea (CT-99) and vanadate in black tea.
Figure 24:
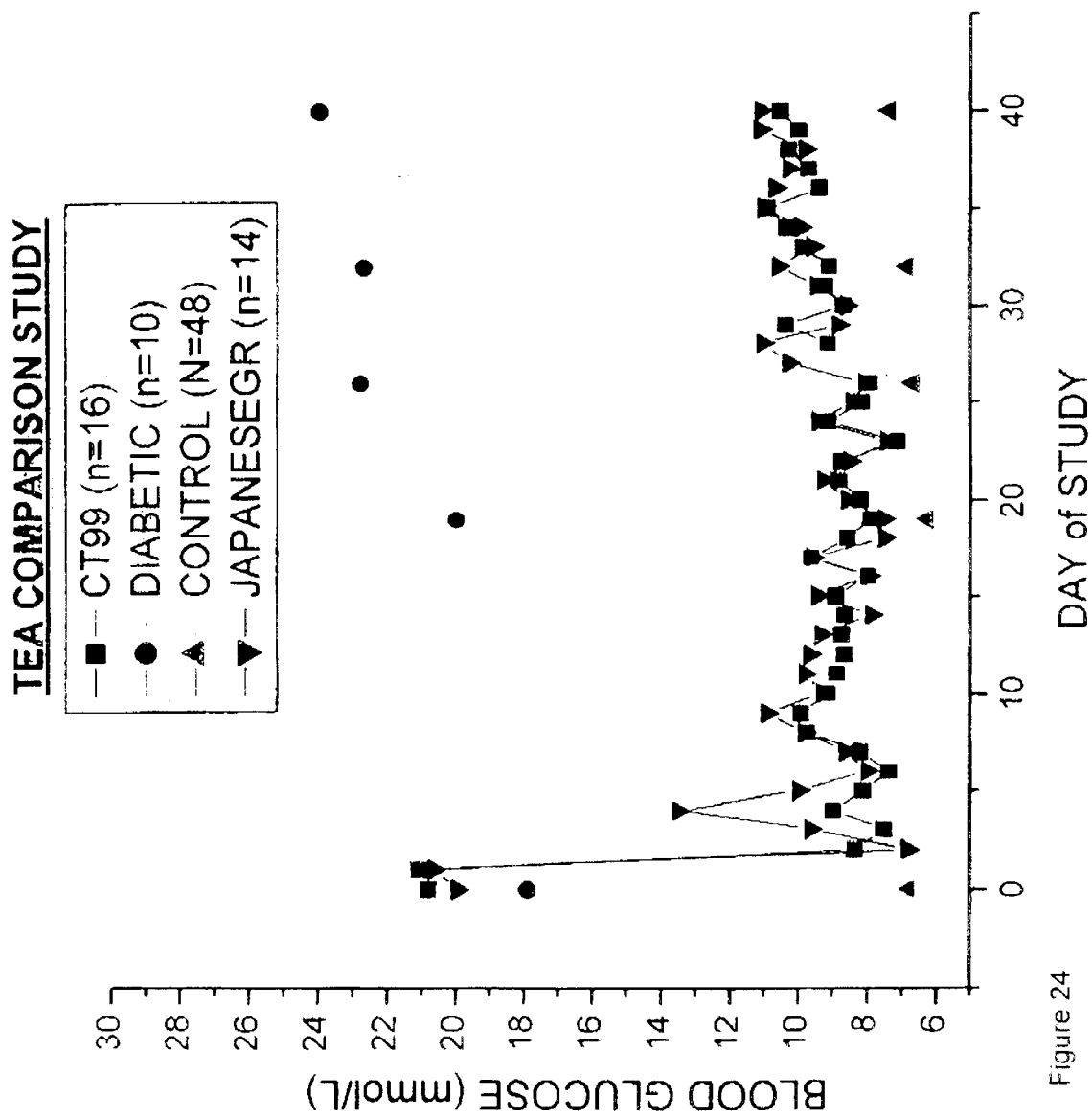
FIG. 24 compares blood glucose levels over time when administered lyophilized vanadate in tea (CT-99) and vanadate in Japanese green tea.
Figure 25:
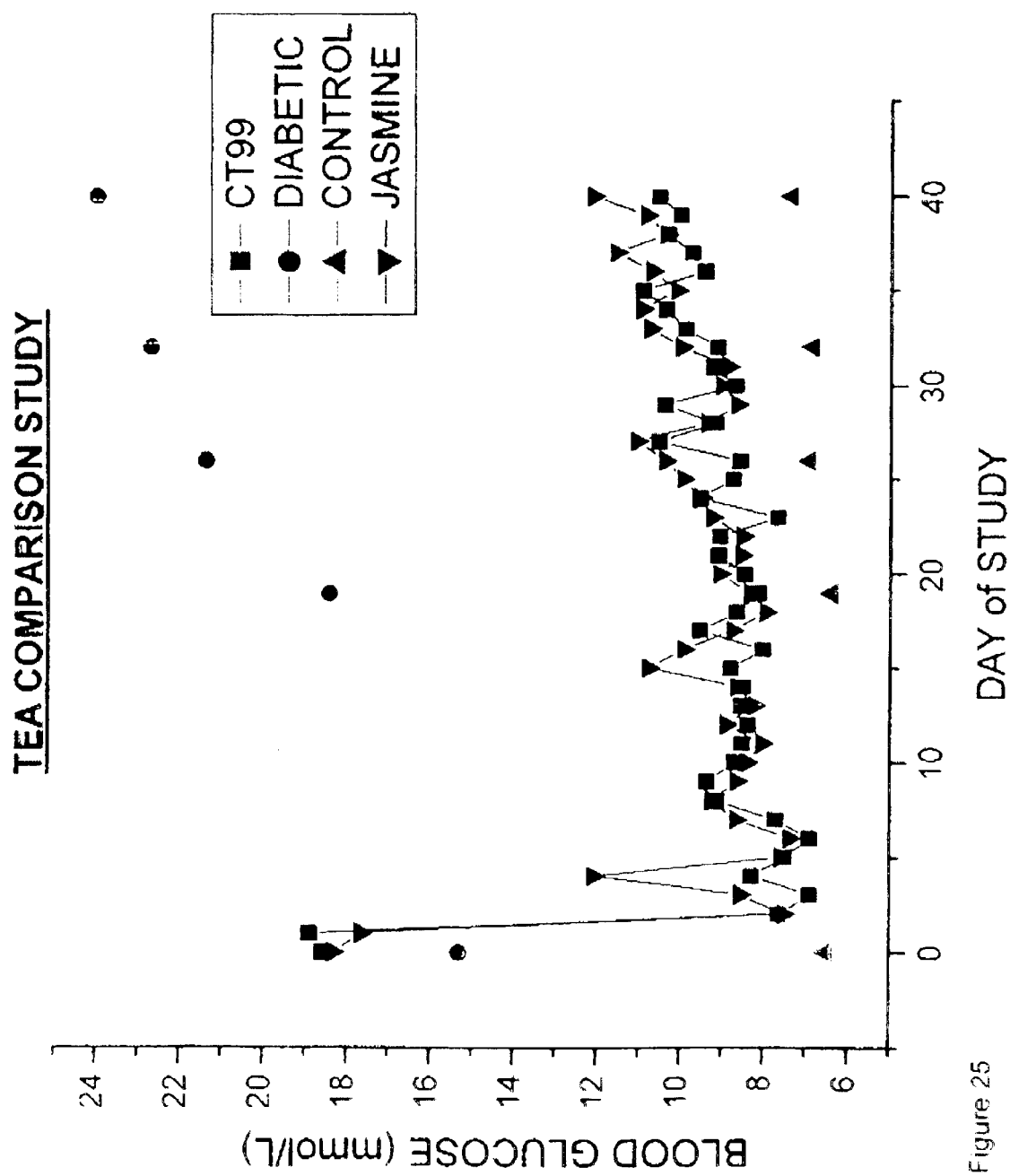
FIG. 25 compares blood glucose levels over time when administered lyophilized vanadate in tea (CT-99) and vanadate in jasmine tea.
Figure 26:
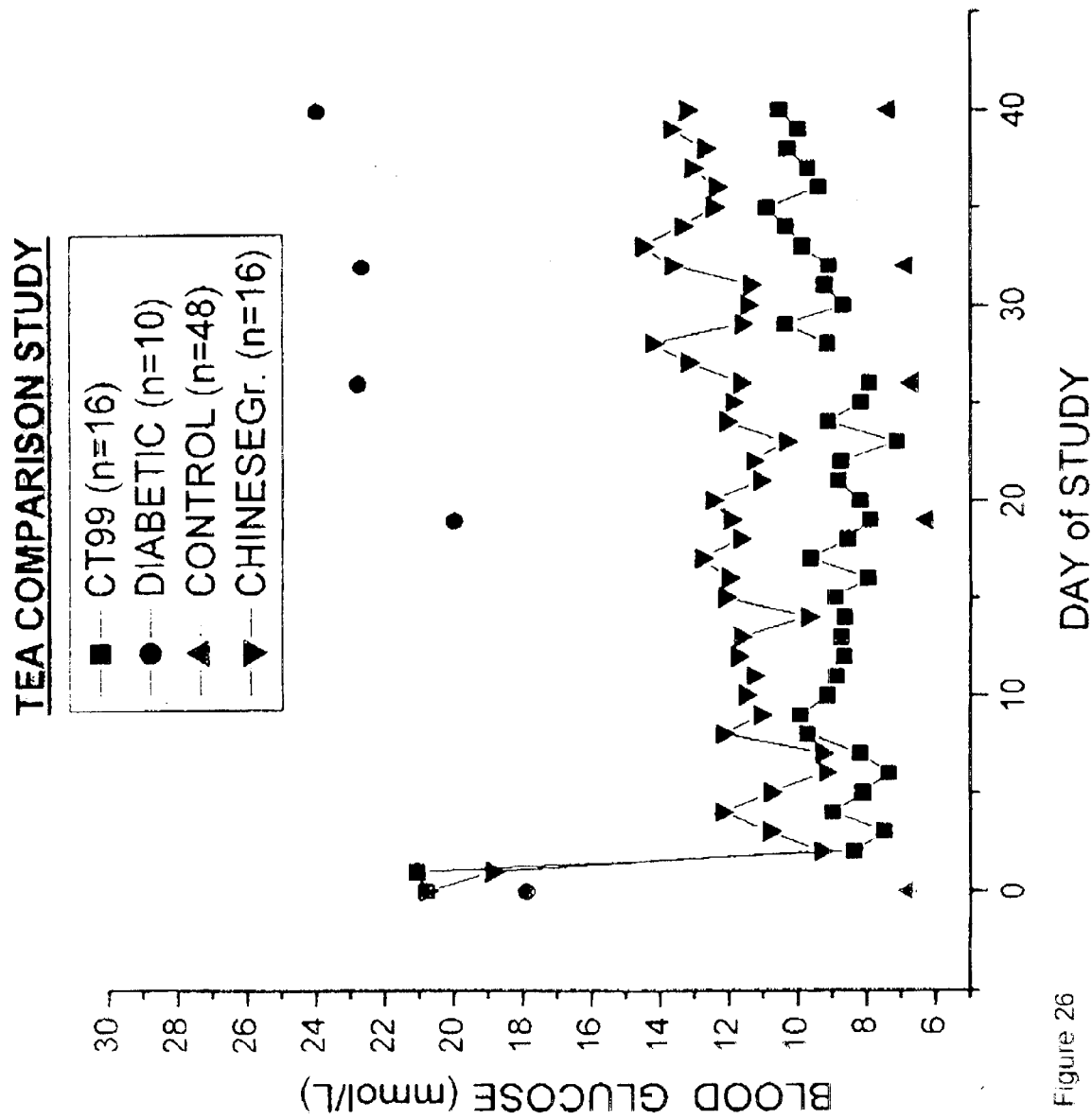
FIG. 26 compares blood glucose levels over time when administered lyophilized vanadate in tea (CT-99) and vanadate in Chinese green tea.
Figure 27:
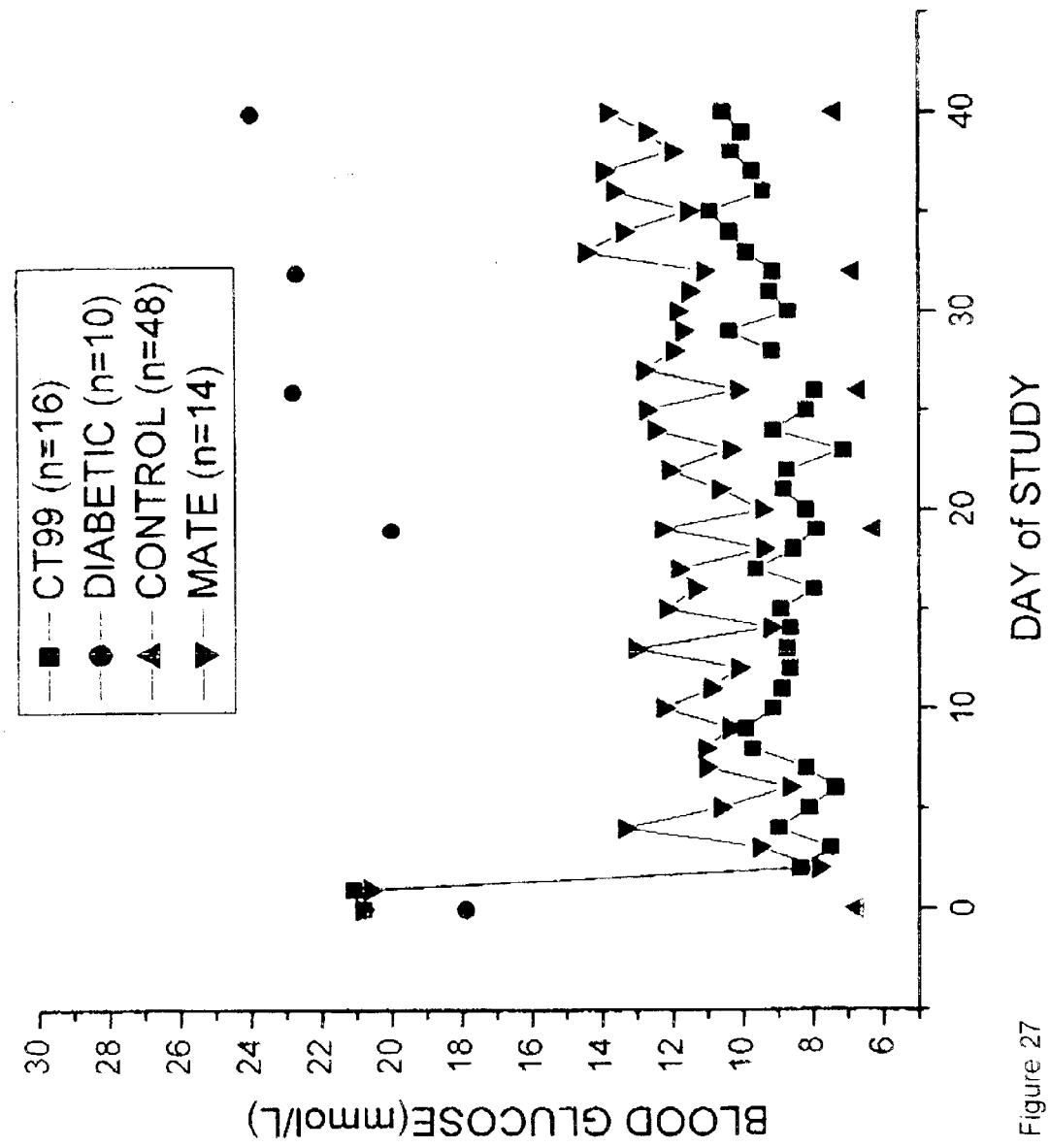
FIG. 27 compares blood glucose levels over time when administered lyophilized vanadate in tea (CT-99) and vanadate in Mate tea.

Similarly, as shown in FIG. 20, raspberry tea did not prevent diarrhea or death in a significant percentage of animals, as did NABOB™ tea, a commercially available brand of tea (see FIGS. 21 and 22).

As can be seen in FIGS. 23–27, lyophilized vanadate in tea prepared as described above, vanadate in black tea, vanadate in Japanese green tea, and vanadate in jasmine tea all lowered blood glucose levels to normalcy. However, vanadate in Chinese green tea and vanadate in Mate tea resulted in somewhat elevated blood glucose levels.

While the preferred embodiments of the invention have been described above, it will be recognized and understood that various modifications may be made therein, and the appended claims are intended to cover all such modifications which may fall within the spirit and scope of the invention.

TABLE 1

VANADATE STUDY
PARAMETER: 30 mg Vanadate in Water

| Rat | No. of Gavages | Last Gavage | Period Without Gavage | Physical Condition | Other |
|---|---|---|---|---|---|
| 37 Red |  |  |  |  | Died: Diarrhea |
| 37 None | 7 maximum | Mar. 29 | <1 week | very good | Difficult to control. Blood glucose still elevated after last gavage (#7) |
| 38 Red | 2 | Feb. 27 | 5 weeks | very good | March 29 = Last blood glucose measurement: Normal |
| 38 None | 5 | Mar. 29 | <1 week | very good | Usually responds to vanadate, but remains normal for only a few days. March 30 = Last measurement: Normal |
| 39 Red | 2 | Feb. 27 | 5 weeks | very good | March 29 = Last blood glucose measurement: Normal |
| 39 None |  |  |  |  | Died: Diarrhea |

TABLE 2

PARAMETER: 40 mg Vanadate in Water

| Rat | No. of Gavages | Last Gavage | Period Without Gavage | Physical Condition | Other |
|---|---|---|---|---|---|
| 34 Red |  |  |  |  | Died: Diarrhea |
| 34 None | 6 | Mar. 29 | <1 week | very good | Always responds to vanadate, but remains normal only for a few days. March 30 = Last measurement: Normal |
| 35 Red |  |  |  |  | Died: Diarrhea |
| 35 None |  |  |  |  | Died: Diarrhea |
| 36 Red | 2 | Feb. 27 | 5 weeks | very good | March 29 = Last blood glucose measurements: Normal |
| 36 None | 6 | Mar. 29 | <1 week | very good | Difficult to control. Blood glucose still elevated. |

TABLE 3

VANADATE STUDY
PARAMETER: 50 mg Vanadate in Water

| Rat | No. of Gavages | Last Gavage | Period Without Gavage | Physical Condition | Other |
|---|---|---|---|---|---|
| 31 Red |  |  |  |  | Died: Diarrhea |
| 31 None | 6 | Mar. 29 | <1 week | very good | Always responds to vanadate, but remains normal only for about 2 days. March 30 = Last blood glucose measurement: Normal |
| 32 Red |  |  |  |  | Died: Diarrhea |
| 32 None |  |  |  |  | Died: Diarrhea |
| 33 Red | 5 | Mar. 29 | 1 week | very good | Usually responds to vanadate, but remained elevated after last gavage (#7). |
| 33 None | 3 | Mar. 22 | 3 weeks | very good | March 29 = Last blood glucose measurements: Normal |

TABLE 4

VANADATE STUDY
PARAMETER: 30 mg Vanadate & Green Tea

| Rat | No. of Gavages | Last Gavage | Period Without Gavage | Physical Condition | Other |
|---|---|---|---|---|---|
| 13 Red | 7 maximum | Mar. 29 | <1 week | very good | Blood glucose still elevated: March 30 |
| 13 None | 6 | Mar. 29 | <1 week | very good | Blood glucose still elevated: March 30 |
| 14 Red | not diabetic |  |  |  | No response to STZ |
| 14 None | not diabetic |  |  |  | No response to STZ |

TABLE 4-continued

VANADATE STUDY
PARAMETER: 30 mg Vanadate & Green Tea

| Rat | No. of Gavages | Last Gavage | Period Without Gavage | Physical Condition | Other |
|---|---|---|---|---|---|
| 15 Red | not diabetic | | | | No response to STZ |
| 15 None | not diabetic | | | | No response to STZ |
| 16 Red | 7 maximum | | <1 week | very good | Blood glucose still elevated: March 30 |
| 16 None | 7 maximum | | <1 week | very good | Blood glucose still elevated: March 30 |

TABLE 5

VANADATE STUDY
PARAMETER: 40 mg Vanadate & Green Tea

| Rat | No. of Gavages | Last Gavage | Period Without Gavage | Physical Condition | Other |
|---|---|---|---|---|---|
| 10 Red | 6 | Mar. 29 | <1 week | very good | Blood glucose still elevated: March 30 |
| 10 None | | | | | Died: Diarrhea |
| 11 Red | 3 | Mar 17 | 3 weeks | very good | March 29 = Last blood glucose measurement: Normal |
| 11 None | 2 | Feb. 27 | 5 weeks | very good | March 29 = Last blood glucose measurement: Normal |
| 12 Red | 7 maximum | Mar 29 | <1 week | | Blood glucose still elevated: March 30 |
| 12 None | 3 | Mar 23 | 3 weeks | | No Gavage required for 3 weeks. March 29 = Last blood glucose measurement: Normal |

TABLE 6

VANADATE STUDY
PARAMETER: 50 mg Vanadate & Green Tea

| Rat | No. of Gavages | Last Gavage | Period Without Gavage | Physical Condition | Other |
|---|---|---|---|---|---|
| 6 Red | 2 | Feb. 27 | 5 weeks | very good | March 29 = Last blood glucose measurement: Normal. Mild diabetes at start of study. |
| 6 None | 2 | Feb. 27 | 5 weeks | very good | March 29 = Last blood glucose measurement: Normal |
| 7 Red | 7 maximum | Mar. 29 | <1 week | very good | Blood glucose still elevated: March 30 |
| 7 None | 3 | Mar. 29 | 4 weeks | very good | No gavage for 4 weeks. Required 7th gavage. |
| 8 Red | 2 | Feb. 27 | 5 weeks | very good | March 29 = Last blood glucose measurement |
| 8 None | 7 maximum | Mar. 29 | <1 week | very good | Blood glucose still elevated: March 30 |
| 9 Red | 6 | Mar. 29 | <1 week | very good | Blood glucose still elevated March 30 |
| 9 None | | | | | Died: Diarrhea |

TABLE 7

VANADATE STUDY
PARAMETER: 30 mg Vanadate & Black Tea

| Rat | No. of Gavages | Last Gavage | Period Without Gavage | Physical Condition | Other |
|---|---|---|---|---|---|
| 46 red | 2 | Feb. 27 | 5 weeks | very good | March 29 = Last blood glucose measurement: Normal |
| 46 None | not diabetic | | | | Did not respond to STZ |

TABLE 7-continued

VANADATE STUDY
PARAMETER: 30 mg Vanadate & Black Tea

| Rat | No. of Gavages | Last Gavage | Period Without Gavage | Physical Condition | Other |
|---|---|---|---|---|---|
| 47 Red | 2 | Feb. 27 | 5 weeks | very good | March = Last blood glucose measurement: Normal. Mildly diabetic at start of study. |
| 47 None | not diabetic | | | | Did not respond to STZ |
| 48 Red | 7 maximum | Mar. 29 | <1 week | very good | Difficult to control. Blood glucose still elevated after last gavage (#7) |
| 48 None | 7 maximum | Mar. 29 | <1 week | very good | Difficult to control. Blood glucose finally normal after last gavage (#7) |
| 49 Red | 2 | Feb. 27 | 5 weeks | very good | March 29 = Last blood glucose measurement: Normal |
| 49 None | 2 | Feb. 27 | 5 weeks | very good | March 29 = Last blood glucose measurement: Normal |
| 50 Red | 2 | Feb. 27 | 5 weeks | very good | March 29 = Last blood glucose measurement: Normal. Mild diabetes at start of study. |
| 50 None | 2 | Feb. 27 | 5 weeks | very good | March 29 = Last blood glucose measurement: Normal. Mild diabetes at start of study. |
| 51 Red | 2 | Feb. 27 | 5 weeks | very good | March 29 = Last blood glucose measurement: Normal. Mild diabetes at start of study. |
| 51 None | 7 maximum | | <1 week | very good | Always responds to Vanadate. Remains normal only for few days. Initial blood glucose: very high. Treatment required to reverse the subsequent slightly elevated levels. March 29 = Last measurement: Normal |

TABLE 8

VANADATE STUDY
PARAMETER: 40 mg Vanadate & Black Tea

| Rat | No. of Gavages | Last Gavage | Period Without Gavage | Physical Condition | Other |
|---|---|---|---|---|---|
| 52 Red | 2 | Feb. 27 | 5 weeks | very good | March 29 = Last blood glucose measurement: Normal. Mild diabetes at start of study. |
| 52 None | 3 | Mar. 08 | 3 weeks | very good | March 29 = Last blood glucose measurement: Normal |
| 53 Red | 2 | Feb. 27 | 5 weeks | very good | March 29 = Last blood glucose measurement: Normal. Mild diabetes at start of study. |
| 53 None | 2 | Feb. 27 | 5 weeks | very good | March 29 = Last blood glucose measurement: Normal |
| 54 Red | 2 | Feb. 27 | 5 weeks | very good | March 29 = Last blood glucose measurement: Normal. Mild diabetes at start of study. |
| 54 None | 3 | Mar. 08 | 3 weeks | very good | March 29 = Last blood glucose measurement: Normal |
| 55 Red | | | | | Died: Diarrhea |
| 55 None | 2 | Feb. 27 | 5 weeks | very good | March 29 = Last blood glucose measurement: Normal. Mild diabetes at start of study. |
| 56 Red | 3 | Mar. 23 | 3 weeks | very good | March 29 = Last blood glucose Measurement: Normal |
| 56 None | 3 | Mar. 08 | 3 weeks | very good | March 29 = Last blood glucose measurement: Normal |

TABLE 9

VANADATE STUDY
PARAMETER: 50 mg Vanadate & Black Tea

| Rat | No. of Gavages | Last Gavage | Period Without Gavage | Physical Condition | Other |
|---|---|---|---|---|---|
| 40 Red | 2 | Feb. 27 | 5 weeks | very good | March 29 = Last blood glucose measurement: Normal |
| 40 None | | | | | Died: Diarrhea |
| 41 Red | 7 maximum | Mar. 29 | <1 week | very good | Usually responds to Vanadate. Blood glucose still elevated after last gavage (#7) |
| 41 None | | | | | Died: Diarrhea |
| 42 Red | 2 | Feb. 27 | 5 weeks | very good | March 29 = Last blood glucose measurement: Normal |
| 42 None | 3 | Mar. 08 | 3 weeks | very good | March 29 = Last blood gluscose measurement: Normal |
| 43 Red | 2 | Feb. 27 | 5 weeks | very good | March 29 = Last blood glucose measurement: Normal |
| 43 None | 3 | Mar. 08 | 3 weeks | very good | March 29 = Last blood glucose measurement: Normal |
| 44 Red | 7 maximum | Mar. 29 | <1 week | very good | Always responds to vanadate, but remains normal for only a few days. March 30 = Last measurement: slightly elevated. |
| 44 None | | | | | Died: Diarrhea |
| 45 Red | 2 | Feb. 27 | 5 weeks | very good | March 29 = last blood glucose measurement: Normal |
| 45 None | | | | | Died (due to gavage procedure) |

What is claimed is:

1. A pharmaceutical composition comprising a therapeutically affective amount of vanadate suspended in decocted black tea, jasmine tea or Japanese green tea for lowering level of blood glucose in an individual wherein said effective amount of vanadate is in range of about 15 mg/mL to 50 mg/mL of decocted tea.

2. The pharmaceutical composition according to claim 1 wherein the tea is jasmine tea.

3. The pharmaceutical composition according to claim 1 wherein the tea is black tea.

4. The pharmaceutical composition according to claim 1 wherein the tea is Japanese green tea.

5. The pharmaceutical composition according to claim 1 wherein the vanadate suspended in decocted tea is lyophilized.

* * * * *